United States Patent
Wacher et al.

(10) Patent No.: US 12,048,735 B2
(45) Date of Patent: *Jul. 30, 2024

(54) ALKALINE PHOSPHATASE FORMULATIONS

(71) Applicant: Theriva Biologics, Inc., Rockville, MD (US)

(72) Inventors: Vincent Wacher, Rockville, MD (US); J. Blair West, Rockville, MD (US); Michael Kaleko, Rockville, MD (US); Christian Furlan Freguia, Rockville, MD (US)

(73) Assignee: Theriva Biologics, Inc., Rockville, MD (US)

( * ) Notice: Subject to any disclaimer, the term of this patent is extended or adjusted under 35 U.S.C. 154(b) by 687 days.

This patent is subject to a terminal disclaimer.

(21) Appl. No.: 17/215,270

(22) Filed: Mar. 29, 2021

(65) Prior Publication Data

US 2021/0220448 A1 Jul. 22, 2021

Related U.S. Application Data

(63) Continuation of application No. 16/037,612, filed on Jul. 17, 2018, now Pat. No. 10,987,410, which is a continuation of application No. PCT/US2018/023327, filed on Mar. 20, 2018.

(60) Provisional application No. 62/474,147, filed on Mar. 21, 2017.

(51) Int. Cl.
| | | |
|---|---|---|
| *A61K 38/46* | (2006.01) | |
| *A61K 9/00* | (2006.01) | |
| *A61K 9/16* | (2006.01) | |
| *A61K 9/20* | (2006.01) | |
| *A61K 9/28* | (2006.01) | |
| *A61K 35/74* | (2015.01) | |
| *A61K 35/741* | (2015.01) | |
| *A61K 47/02* | (2006.01) | |
| *A61K 47/12* | (2006.01) | |
| *A61K 47/38* | (2006.01) | |
| *A61P 1/00* | (2006.01) | |
| *C12N 9/16* | (2006.01) | |

(52) U.S. Cl.
CPC .......... *A61K 38/465* (2013.01); *A61K 9/0095* (2013.01); *A61K 9/1694* (2013.01); *A61K 9/2009* (2013.01); *A61K 9/2054* (2013.01); *A61K 9/2077* (2013.01); *A61K 9/2846* (2013.01); *A61K 35/74* (2013.01); *A61K 35/741* (2013.01); *A61K 47/02* (2013.01); *A61K 47/12* (2013.01); *A61K 47/38* (2013.01); *A61P 1/00* (2018.01); *C12N 9/16* (2013.01); *C12Y 301/03001* (2013.01)

(58) Field of Classification Search
CPC .. A61K 38/465; A61K 9/0095; A61K 9/1694; A61K 9/2009; A61K 9/2054; A61K 9/2077; A61K 9/2846; A61K 47/02; A61K 47/12; A61K 47/38; A61P 1/00; C12Y 301/03001
See application file for complete search history.

(56) References Cited

U.S. PATENT DOCUMENTS

| | | |
|---|---|---|
| 6,290,952 B1 | 9/2001 | Poelstra et al. |
| 6,686,392 B1 | 2/2004 | Avram et al. |
| 6,884,602 B2 | 4/2005 | Mueller et al. |
| 7,011,965 B2 | 3/2006 | Kiss |
| 7,014,852 B2 | 3/2006 | Kiss |
| 7,048,914 B2 | 5/2006 | Kiss |
| 7,312,198 B2 | 12/2007 | Kiss |
| 7,374,754 B2 | 5/2008 | Kiss |
| 7,501,116 B2 | 3/2009 | Kiss |
| 7,557,081 B2 | 7/2009 | Kiss |
| 7,695,714 B2 | 4/2010 | Kiss |
| 7,718,170 B2 | 5/2010 | Kiss |
| 7,786,082 B2 | 8/2010 | Kiss |
| 7,790,685 B2 | 9/2010 | Kiss |
| 7,858,085 B2 | 12/2010 | Kiss |
| 7,964,188 B2 | 6/2011 | Kiss |
| 8,372,638 B2 | 2/2013 | Kiss |
| 8,460,654 B2 | 6/2013 | Kiss |
| 8,574,863 B2 | 11/2013 | Brands et al. |
| 8,603,464 B2 | 12/2013 | Kiss |
| 8,778,674 B2 | 7/2014 | Kiss |
| 2004/0091530 A1 | 5/2004 | Ende et al. |
| 2007/0280922 A1 | 12/2007 | Kiss |
| 2009/0004281 A1 | 1/2009 | Nghiem et al. |

(Continued)

FOREIGN PATENT DOCUMENTS

| | | |
|---|---|---|
| EP | 1952823 | 8/2008 |
| WO | WO 2004112494 | 12/2004 |

(Continued)

OTHER PUBLICATIONS

Chen, et al. "Identification of specific targets for the gut mucosal defense factor intestinal alkaline phosphatase," American Journal of Physiology, Aug. 2010, Epub May 2012, vol. 299, No. 2 pp. G467-G475.

(Continued)

*Primary Examiner* — Kade Ariani
(74) *Attorney, Agent, or Firm* — Morgan, Lewis & Bockius LLP

(57) ABSTRACT

The present invention provides, in part, formulations comprising an alkaline phosphatase (AP)-based agent. Particularly, modified-release powder formulations comprising an AP-based agent are provided which release a substantial amount of the AP-based agent in the intestines. Therapeutic uses of the formulations are also provided.

7 Claims, 1 Drawing Sheet
Specification includes a Sequence Listing.

(56) References Cited

U.S. PATENT DOCUMENTS

| | | |
|---|---|---|
| 2011/0142817 A1 | 6/2011 | Brands et al. |
| 2012/0308526 A1 | 12/2012 | Ohtake et al. |
| 2013/0280232 A1 | 10/2013 | Brands et al. |
| 2015/0216813 A1 | 8/2015 | Everett et al. |
| 2017/0252327 A1 | 9/2017 | Hodin et al. |

FOREIGN PATENT DOCUMENTS

| | | |
|---|---|---|
| WO | WO 2005055956 | 6/2005 |
| WO | WO 2005074978 | 8/2005 |
| WO | WO 2007055760 | 5/2007 |
| WO | WO 2007081654 | 7/2007 |
| WO | WO 2008024103 | 2/2008 |
| WO | WO 2008094037 | 8/2008 |
| WO | WO 2008104200 | 9/2008 |
| WO | WO 2009106368 | 9/2009 |
| WO | WO 2010025267 | 3/2010 |
| WO | WO 2012054057 | 4/2012 |

OTHER PUBLICATIONS

International Search Report & Written Opinion, PCT/US2018/023327, dated May 25, 2018, 12 pages.

Alshahrani, et al., "Stability-enhanced Hot-melt Extruded Amorphous Solid Dispersions via Combinations of Soluplus® and HPMCAS-HF," American Association of Pharmaceutical Scientists, vol. 16, No. 4, pp. 824-834, Aug. 2015.

Beumer, et al., "Calf Intestinal Alkaline Phosphatase, A Novel Therapeutic Drug for Lipopolysaccharide (LPS)-Mediated Diseases, Attenuates LPS Toxicity in Mice and Piglets," The Journal of Pharmacology and Experimental Therapeutics, vol. 307, No. 2, pp. 737-744 (Jul. 2003).

Chen, et al., "A Role for Intestinal Alkaline Phosphatase in the Maintenance of Local Gut Community," Dig Dis Sci. Apr. 2011; 56(4): 1020-1027 (doi:10.1007/s10620-010-1396-x).

Curatolo, et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, pp. 1419-1431 (Jun. 2009).

Economopoulos, et al., "Prevention of antibiotic-associated metabolic syndrome in mice by intestinal alkaline phosphatase," Diabetes, Obesity and Metabolism, vol. 18, No. 5., pp. 519-527 (May 2016).

Estaki, et al., "Interplay between intestinal alkaline phosphatase, diet, gut microbes and immunity," World Journal of Gastroenterology, 20(42), pp. 15650-15656 (Nov. 2014).

Friesen, et al., "Hydroxypropyl Methylcellulose Acetate Succinate-Based Spray-Dried Dispersions: An Overview," Molecular Pharmaceuticals, vol. 5, No. 6, pp. 1003-1109 (Dec. 2008).

Goldberg, et al., "Intestinal alkaline phosphatase is a gut mucosal defense factor maintained by enteral nutrition," PNAS, vol. 105, No. 9, pp. 3551-3556 (Mar. 2008).

Kaliannan, et al., "Intestinal alkaline phosphatase prevents metabolic syndrome in mice," PNAS, vol. 110, No. 17, pp. 7003-7008 (Apr. 2013).

Lallès, "Intestinal alkaline phosphatase: novel functions and protective effects," Nutrition Reviews, vol. 72(2), pp. 82-94 (2014).

Malo, et al., "Intestinal alkaline phosphatase preserves the normal homeostasis of gut microbiota," Gut 2010;59:1476-1484 (doi:10.1136/gut.2010.211706).

Parlato, et al., "Human ALPI deficiency causes inflammatory bowel disease and highlights a key mechanism of gut homeostasis," EMBO Molecular Medicine, e8483, pp. 1-12 (Mar. 2018).

Peters, et al., "The Potential of Alkaline Phosphatase as a Treatment for Sepsis-Associated Acute Kidney Injury," Nephron Clin Pract 2014; 127: pp. 144-148 (Sep. 2014).

Shah, et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences, vol. 102, No. 3, pp. 967-981 (Mar. 2013).

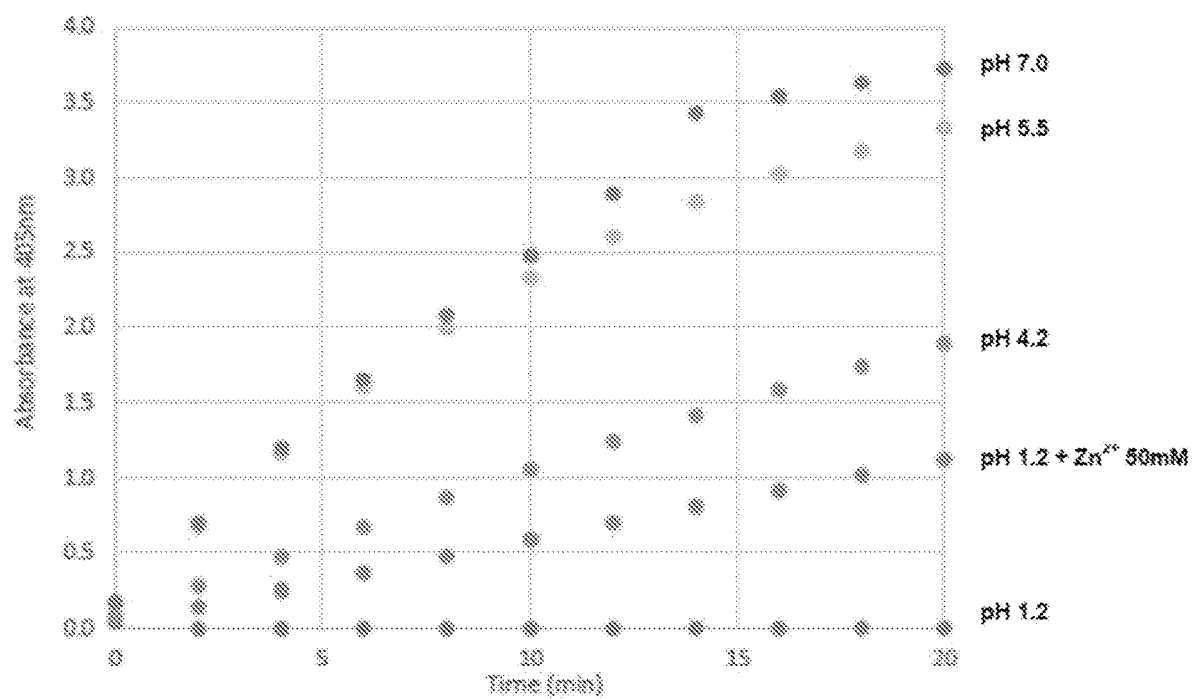

ALKALINE PHOSPHATASE FORMULATIONS

PRIORITY

This application is a continuation application of U.S. patent application Ser. No. 16/037,612, filed Jul. 17, 2018, which is a continuation of International Application No. PCT/US18/23327, filed Mar. 20, 2018, which claims the benefit of U.S. Provisional Application No. 62/474,147, filed Mar. 21, 2017, the contents of which are hereby incorporated by reference herein in their entireties.

SEQUENCE LISTING

The instant application contains a Sequence Listing which has been submitted in ASCII format via EFS-Web and is hereby incorporated by reference in its entirety. The ASCII copy, created Mar. 29, 2021, is 73 KB in size and is named SYN-024C2_sequence listing.txt.

FIELD OF THE INVENTION

The present invention provides, in part, pharmaceutical dosage forms comprising alkaline phosphatase-based agents and uses thereof and methods of treatment for diseases, such as microbiome-related diseases.

BACKGROUND

Alkaline phosphatases are dimeric metalloenzymes that catalyze the hydrolysis of phosphate esters and dephosphorylate a variety of target substrates at physiological and higher pHs. Alkaline phosphatases (APs) are found in prokaryotic as well as in eukaryotic organisms (e.g., in *E. coli* and mammals). Mammalian APs have been shown to play important roles in gut homeostasis, mucosal barrier function, promotion of commensal bacteria, and defense from pathogens. Mammalian APs exert their properties by primarily targeting lipopolysaccharide (LPS, a toll-like receptor-4 (TLR4) agonist), flagellin (a TLR5 agonist) and CpG DNA (a TLR9 agonist). APs also degrade intestine luminal nucleotide triphosphates (NTPs, e.g., ATP, GTP, etc.), which promote the growth of good bacteria and reverses dysbiosis. Accordingly, APs may find clinical use as, for example, microbiome preserving agents for treating various gastrointestinal (GI) disorders.

However, despite its exciting clinical potential, no AP-based drugs have been approved to date.

Further, formulating protein biologics are a particular challenge for treating patients that cannot easily be administered oral drugs. For example, powderizing protein biologics, including APs, is particularly challenging.

There remains a need for novel formulations and therapeutic uses of alkaline phosphatases for therapeutic use.

SUMMARY OF THE INVENTION

Accordingly, in some aspects, the present invention provides modified-release formulations comprising an alkaline phosphatase (AP)-based agent and/or additional therapeutic agent. In various embodiments, the AP-based agent is a mammalian or bacterial alkaline phosphatase. In some embodiments, the AP-based agent is a mammalian alkaline phosphatase. In some embodiments, the AP-based agent is an intestinal alkaline phosphatase. In some embodiments, the AP-based agent is a bacterial alkaline phosphatase. In some embodiments, the bacterial alkaline phosphatase has catalytic activity comparable to that of a mammalian phosphatase.

In various embodiments, the present invention provides modified-release formulations. In various embodiments, the formulation is an oral dosage form comprising powders. In an embodiment, the powders include AP-based agents dispersed in a solid matrix such as a polymeric matrix. In some embodiments, the powdered formulations of the present invention can be added to food (e.g. juices, strained and/or pureed foods (e.g. fruits, vegetables), sauces, infant formulas, milk, etc.). In some embodiments, the powdered formulations of the present invention can be in a sachet. In some embodiments, the formulation may be in the form of a tablet comprising powders. In some embodiments, the formulation may be in the form of a capsule comprising powders. In some embodiments, the tablets or capsules may further comprise an enteric agent. In various embodiments, the present invention provides modified-release formulations suitable for administration to a patient that is unable to receive a pill.

In various embodiments, the formulation is resistant to compression and therefore suitable for tabletting. In various embodiments, the formulation remains substantially stable in gastric fluid such that the AP-based agent is not released in the stomach. In an embodiment, the powders transform into a gel form in the presence of stomach acid. In an embodiment, the formulations release a substantial amount of the AP-based agent in the intestinal tract including the small intestines and/or the large intestines.

In another aspect, the present invention provides methods for the therapeutic use of an AP, including the modified-release formulations comprising AP-based agents. In an embodiment, the present invention provides methods for the treatment of a microbiome-related disorder. In another embodiment, the present invention provides methods for the treatment or prevention of an antibiotic-induced adverse effect in the GI tract and/or a *C. difficile* infection (CDI) and/or a *C. difficile*-associated disease. In another embodiment, the present invention provides methods for the treatment of a metabolic disorder such as obesity, diabetes, and/or a metabolic syndrome. In another embodiment, the present invention provides methods for the treatment of a neurological disease. Methods for treating sepsis and renal failure are also provided. In a further embodiment, the present invention provides methods for the treatment of HIV-mediated gut dysbiosis and/or GI barrier dysfunction.

DESCRIPTION OF THE FIGURES

FIG. 1 depicts sensitivity of intestinal alkaline phosphatase (IAP) activity to pH. IAP was incubated at the indicated pH for 1 hour then a sample of the IAP solution diluted to pH 9.2 and activity measured using a colorimetric assay (cleavage of p-nitrophenol phosphate). To measure the reversibility of acid effects, a separate sample was neutralized to pH 7.2 with either Tris or HEPES recovery buffer and incubated for a further 1.5 hours prior to measurement of IAP activity. The percentage of IAP activity recovered for each pH condition after the additional 1.5 hours incubation in Tris buffer was: pH 1.2 0%; pH 4.2 42%; pH 5.5 58% and pH 7.0 110%, indicating deactivation at pH 1.2 was irreversible. When $Mg^{2+}$ (1 mM) and $Zn^{2+}$ (0.1 mM) were added to the HEPES recovery buffer, 100% of the IAP activity could be recovered after preincubation at pH 4.0 or pH 5.0.

DETAILED DESCRIPTION OF THE INVENTION

Alkaline Phosphatase-Based Agents

The present invention is directed, in part, to pharmaceutical compositions, formulations, and uses of one or more alkaline phosphatase-based agents (AP-based agents). Illustrative AP-based agents that may be utilized in the present invention include, but are not limited to, intestinal alkaline phosphatase (IAP; e.g., calf IAP or bovine IAP, chicken IAP, goat IAP), placental alkaline phosphatase (PLAP), placental-like alkaline phosphatase, germ cell alkaline phosphatase (GCAP), non-tissue specific alkaline phosphatase (TNAP; which is primarily found in the liver, kidney, and bone), bone alkaline phosphatase, liver alkaline phosphatase, kidney alkaline phosphatase, bacterial alkaline phosphatase, fungal alkaline phosphatase, shrimp alkaline phosphatase, modified IAP, recombinant IAP, or any polypeptide comprising alkaline phosphatase activity.

In various embodiments, the present invention contemplates the use of mammalian alkaline phosphatases including, but not limited to, intestinal alkaline phosphatase (IAP), placental alkaline phosphatase (PLAP), germ cell alkaline phosphatase (GCAP), and the tissue non-specific alkaline phosphatase (TNAP).

In some embodiments, the AP-based agent is IAP. IAP is produced in the proximal small intestine and is bound to the enterocytes via a glycosyl phosphatidylinositol (GPI) anchor. Some IAP is released into the intestinal lumen in conjunction with vesicles shed by the cells and as soluble protein stripped from the cells via phospholipases. The enzyme then traverses the small and large intestine such that some active enzyme can be detected in the feces. In an embodiment, the IAP is human IAP (hIAP). In an embodiment, the IAP is calf IAP (cIAP), also known as bovine IAP (bIAP). There are multiple isozymes of bIAP, for example, with bIAP II and IV having higher specific activity than bIAP I. In an embodiment, the IAP is any one of the cIAP or bIAP isozymes (e.g., bIAP I, II, and IV). In an embodiment, the IAP is bIAP II. In another embodiment, the IAP is bIAP IV.

In various embodiments, the AP-based agent is hIAP or a variant thereof. In some embodiments, the AP-based agent is hIAP comprising the amino acid sequence of SEQ ID NO:1 as depicted below.

HIAP

SEQ ID NO: 1

```
  1 mqgpwvllll glrlqlslgv ipaeeenpaf wnrqaaeald aakklqpiqk vaknlilflg
 61 dglgvptvta trilkgqkng klgpetplam drfpylalsk tynvdrqvpd saatataylc
121 gvkanfqtig lsaaarfnqc nttrgnevis vmnrakqagk svgvvtttrv qhaspagtya
181 htvnrnwysd admpasarge gcqdiatgli snmdidvilg ggrkymfpmg tpdpeypada
241 sqngirldgk nlvqewlakh qgawyvwnrt elmqasldqs vthlmglfep gdtkyeihrd
301 ptldpslmem teaalrllsr nprgfylfve ggridhghhe gvayqaltea vmfddaiera
361 gqltseedtl tlvtadhshv fsfggytlrg ssifglapsk aqdskaytsi lygngpgyvf
421 nsgvrpdvne sesgspdyqq qaavplsset hggedvavfa rgpqahlvhg vqeqsfvahv
481 mafaaclepy tacdlappac ttdaahpvaa slpllagtll llgasaap
```

Without wishing to be bound by theory, it is believed that a cysteine at the carboxy terminus of the AP-based agent (e.g., at position 500 of SEQ ID NO:1) may interfere with protein folding. Accordingly, in some embodiments, the AP-based agent includes a mutation of the cysteine (e.g., at position 500 of SEQ ID NO:1). In some embodiments, the cysteine is replaced with glycine.

In various embodiments, the AP-based agent is bIAP II or a variant thereof. In an embodiment, the bIAP II comprises the signal peptide and carboxy terminus of bIAP I. In an embodiment, the bIAP II comprises an aspartate at position 248 (similar to bIAP IV). In an embodiment, the bIAP II comprises the amino acid sequence of SEQ ID NO: 2:

BIAP II with 248D assignment—SEQ ID NO:2. The signal peptide and sequence past 480 are derived from bIAP I.

```
  1 mqgacvllll glhlqlslgl ipaeeenpaf wnrqaagald vakklqpiqt aaknvilflg
 61 dgmgvptvta trilkgqmng klgpetplam dqfpyvalsk tynvdrqvpd sagtataylc
121 gvkgnyrtig vsaaarynqc nttrgnevts vinrakkagk avgvvtttrv qhaspagaya
181 htvnrnwysd adlpadaqkn gcqdiaaqlv ynmdidvilg ggrmymfpeg tpdpeypdda
241 svngvrkdkq nlvqewgakh qgagyvwnrt allqaaddss vthlmglfep admkynvqqd
```

```
-continued
301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipdaahl aasppplall agamllllap tly
```

In various embodiments, the AP-based agent is bIAP IV or a variant thereof. In an embodiment, the bIAP IV comprises the amino acid sequence of SEQ ID NO: 3:

```
BIAP IV
                                                          SEQ ID NO: 3
  1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsdaahlaas ppslallaga mllllapaly
```

Mammalian alkaline phosphatases are GPI anchored proteins. They have signal peptides and are translated into the secretory pathway. Once in the endoplasmic reticulum (ER), the proteins are glycosylated and folded. There are two disulfide bonds as well as a single free cysteine that is apparently not accessible on the surface. In the late ER, the carboxy terminus is removed and the GPI anchor is appended. GPI anchoring is therefore a process that occurs at the carboxy terminus of the alkaline phosphatase. The inclusion of stop codons at the anchor site enables secretion of biologically active protein (presumably the homodimer). While there is no consensus sequence, the carboxy terminus includes three amino acids, termed omega, omega+1, and omega+2 which are followed by a short stretch of hydrophilic amino acids and then a stretch of hydrophobic amino acids. Without wishing to be bound by theory, it is believed that the hydrophobicity is critical for embedding the carboxy terminus in the ER membrane. There an enzymatic reaction replaces the carboxy terminus with the GPI anchor.

Within hPLAP, the GPI anchor is attached at an aspartate in the sequence, DAAH. Similarly, hIAP, bIAP II, and bIAP IV also have this DAAH sequence conserved, potentially serving as the GPI anchor site. Mutational studies with hPLAP indicate that preventing GPI anchoring results in intracellular retention. In addition, mutations around the anchor site or in the hydrophobic domain either 1) prevent anchor attachment leading to intracellular retention or 2) do not block anchor attachment. Without wishing to be bound by theory, it is believed that the hydrophobic domain serves as a signal for GPI anchor attachment. Truncating or eliminating the hydrophobic domain leads to secretion. Finally, there is a single mutation in the hydrophobic domain that, in hPLAP, enables secretion of the protein with its hydrophobic domain intact.

In other embodiments, the AP-based agent of the invention is a secreted protein. In some embodiments, the AP-based agent is not GPI anchored. In some embodiments, the AP-based agent may lack the GPI anchor site. In some embodiments, the AP-based agent comprises a stop codon that is inserted immediately after the GPI anchor site. In an embodiment, the AP-based agent comprises a stop codon after the aspartate in the DAAH consensus site (e.g., at amino acid 503 of hIAP and bIAP IV or amino acid 506 of bIAP II).

```
              HIAP with stop codon
                                                          (SEQ ID NO: 4)
  1 mqgpwvllll glrlqlslgv ipaeeenpaf wnrqaaeald aakklqpiqk vaknlilflg 61 dglgvptvta trilkgqkng klgpetplam drfpylalsk tynvdrqvpd saatataylc 121 gvkanfqtig lsaaarfnqc nttrgnevis vmnrakqagk svgvvtttrv qhaspagtya 181 htvnrnwysd admpasarge gcqdiatgli snmdidvilg ggrkymfpmg tpdpeypada 241 sqngirldgk nlvqewlakh qgawyvwnrt elmqasldqs vthlmglfep gdtkyeihrd 301 ptldpslmem teaalrllsr nprgfylfve ggridhghhe gvayqaltea vmfddaiera 361 gqltseedtl tlvtadhshv fsfggytlrg ssifglapsk aqdskaytsi lygngpgyvf
```

-continued

```
421 nsgvrpdvne sesgspdyqq qaavplsset hggedvavfa rgpqahlvhg vqeqsfvahv 481 mafaaclepy tacdlappag ttd
```

BIAP II with stop codon (SEQ ID NO: 5)
```
  1 mqgacvllll glhlqlslgl ipaeeenpaf wnrqaaqald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcqdiaaqlv ynmdidvilg ggrmymfpeg tpdpeypdda 241 svngvrkdkq nlvqewqakh qgagyvwnrt allqaaddss vthlmglfep admkynvqqd 301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipd
```

BIAP IV with stop codon (SEQ ID NO: 6)
```
  1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewgakh qgagyvwnrt ellgaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsd
```

In an embodiment, the AP-based agent is bIAP IV and includes a stop codon after amino acid 508 to mimic a secreted PLAP construct as depicted below:

BIAP IV with stop codon after amino acid 508

(SEQ ID NO: 7)
```
  1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewgakh qgagyvwnrt ellgaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsdaahla
```

In various embodiments, the AP-based agent of the invention is a fusion protein. In some embodiments, the AP-based agent comprises an alkaline phosphatase fused to a protein domain that replaces the GPI anchor sequence. In some embodiments, the alkaline phosphatase is fused to a protein domain that promotes protein folding and/or protein purification and/or protein dimerization and/or protein stability. In various embodiments, the AP-based agent fusion protein has an extended serum half-life.

In an embodiment, the alkaline phosphatase is fused to an immunoglobulin Fc domain and/or hinge region. In various embodiments, the immunoglobulin Fc domain and/or hinge region is derived from the Fc domain and/or hinge region of an antibody (e.g., of IgG, IgA, IgD, and IgE, inclusive of subclasses (e.g. IgG1, IgG2, IgG3, and IgG4, and IgA1 and IgA2)). In an embodiment, the AP-based agent of the invention comprises an alkaline phosphatase fused to the hinge region and/or Fc domain of IgG.

In various embodiments, the AP-based agent is fused to a Fc domain of IgG comprising one or more mutations. In some embodiments, the one or more mutations in the Fc domain of IgG function to increase serum half-life and longevity. In some embodiments, the Fc domain of IgG comprises one or more mutations at amino acid residues 251-256, 285-290, 308-314, 385-389 and 428-436, numbered according to the EU index as in Kabat (see Kabat et al., (1991) Sequences of Proteins of Immunological Interest, U.S. Public Health Service, National Institutes of Health, Washington, DC). In some embodiments, at least one of the amino acid substitutions in the Fc domain of IgG is at amino acid residue 252, 254, 256, 309, 311, 433 or 434. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain of IgG comprises one or more mutations at amino acid residue 252, 254, 256, 433, 434, or 436. In an embodiment, the Fc domain of IgG includes a triple M252Y/S254T/T256E mutation or YTE mutation. In another embodiment, the Fc domain of IgG includes a triple H433K/N434F/Y436H mutation or KFH mutation. In a further embodiment, the Fc domain of IgG includes a YTE and KFH mutation in combination. Additional exemplary mutations in the Fc domain of IgG are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, and U.S. Pat. No. 7,083,784, the entire contents of which are hereby incorporated by reference. In various embodiments, the one or more mutations in the Fc domain of IgG increases affinity for the neonatal Fc receptor (FcRn). In some embodiments, the one or more mutations in the Fc domain of IgG increases affinity for FcRn at a pH of about 6.0, about 6.1, about 6.2, about 6.3, about 6.4, or about 6.5.

In various embodiments, the alkaline phosphatase is fused to one or more of PEG, XTENylation (e.g. as rPEG), polysialic acid (POLYXEN), albumin, elastin-like protein, elastin like protein (ELP), PAS, HAP, GLK, CTP, and transferrin. In various embodiments, the alkaline phosphatase is fused to one or more of the agents described in BioDrugs (2015) 29:215-239, the entire contents of which are hereby incorporated by reference.

In an embodiment, the alkaline phosphatase is fused to a protein domain (e.g., an immunoglobulin Fc domain) via a linker to the GPI anchor site. For example, the alkaline phosphatase may be fused to a protein domain via the aspartate at the GPI anchor sequence. The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present AP-based agent. In another example, the linker may function to target the AP-based agent to a particular cell type or location.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). In an embodiment, the linker sequence is GGSGGSGGGGSGGGGS (SEQ ID NO: 18). Additional illustrative linkers include, but are not limited to, linkers having the sequence LE, GGGGS (SEQ ID NO: 19), (GGGGS)$_n$ (n=2-4) (SEQ ID NOs: 20-22), (Gly)$_8$ (SEQ ID NO: 23), (Gly)$_6$ (SEQ ID NO: 24), (EAAAK)$_n$ (n=1-3) (SEQ ID Nos: 25-27), A(EAAAK)$_n$A (n=2-5) (SEQ ID Nos: 28-31), AEAAAKEAAAKA (SEQ ID NO: 28), A(EAAAK)$_4$ALEA(EAAAK)$_4$A (SEQ ID NO: 32), PAPAP (SEQ ID NO: 33), KESGSVSSEQLAQFRSLD (SEQ ID NO: 34), EGKSSGSGSESKST (SEQ ID NO: 35), GSAGSAAGSGEF (SEQ ID NO: 36), and (XP)$_n$, with X designating any amino acid, e.g., Ala, Lys, or Glu. In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In some embodiments, the linker is a synthetic linker such as PEG.

that the inhibitory function is located to the carboxy terminus that would be relieved upon GPI anchor addition. Alternatively, other activities such as folding or metal (Zn or Mg) inclusion could control activity.

In various embodiments, the AP-based agent of the invention is a pro-enzyme. In an embodiment, the activity of the proenzyme is suppressed by a carboxy terminus. In an

---

Illustrative Fc fusion constructs of the invention include:

BIAP II with Fc Fusion (SEQ ID NO:8) - Fc domain is underlined

```
  1 mqgacvllll glhlqlslgl ipaeeenpaf wnrgaagald vakklqpiqt aaknvilflg
 61 dgmgvptvta trilkgqmng klgpetplam dqfpyvalsk tynvdrqvpd sagtataylc
121 gvkgnyrtig vsaaarynqc nttrgnevts vinrakkagk avgvvtttry qhaspagaya
181 htvnrnwysd adlpadaqkn gcqdiaaglv ynmdidvilg ggrmymfpeg tpdpeypdda
241 svngvrkdkq nlvqewqakh qgaqyvwnrt allqaaddss vthlmglfep admkynvqqd
301 htkdptlaem teaalqvlsr nprgfylfve ggridhghhd gkaymaltea imfdnaiaka
361 neltseldtl ilvtadhshv fsfggytlrg tsifglapgk aldsksytsi lygngpgyal
421 gggsrpdvng stseepsyrq qaavplaset hggedvavfa rgpqahlvhg vqeetfvahi
481 mafagcvepy tdcnlpapat atsipdGGSGGSGGGGSGGGGSEPKSCDKTHTCPPCPAPE
    LLGGPSVFLFPPKPKDTLMI SRTPEVTCVVVDVSHEDPQV KFNWYVDGVQVHNAKTKPRE
    QQYNSTYRVVSVLTVLHQNW LDGKEYKCKVSNKALPAPIE KTISKAKGQPREPQVYTLPP
    SREEMTKNQVSLTCLVKGFY PSDIAVEWESNGQPENNYKT TPPVLDSDGSFFLYSKLTVD
    KSRWQQGNVFSCSVMHEALH NHYTQKSLSLSPGK
```

BIAP IV with Fc Fusion (SEQ ID NO: 9) - Fc domain is underlined

```
  1 mqwacvllll glwlqlsltf ipaeeedpaf wnrgaagald vakklqpiqt aaknvilflg
 61 dgmgvptvta trilkgqmng klgpetplam dqfpyvalsk tynvdrqvpd sagtataylc
121 gvkgnyktig vsaaarynqc nttsgnevts vmnrakkagk svgvvttsry qhaspagaya
181 htvnrnwysd adlpadaqty gcqdiatqlv nnmdidvilg ggrmymfpeg tpdpeypydv
241 nqtgvrkdkr nlvqewqakh qgaqyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lygngpgyvl
421 ggglrpdvnd sisedpsyrq qaavplsses hggedvavfa rgpqahlvhg vqeetfvahv
481 mafagcvepy tdcnlpapsg lsdGGSGGSGGGGSGGGGSEPKSCDKTHTCPPCPAPE
    LLGGPSVFLFPPKPKDTLMI SRTPEVTCVVVDVSHEDPQV KFNWYVDGVQVHNAKTKPRE
    QQYNSTYRVVSVLTVLHQNW LDGKEYKCKVSNKALPAPIE KTISKAKGQPREPQVYTLPP
    SREEMTKNQVSLTCLVKGFY PSDIAVEWESNGQPENNYKT TPPVLDSDGSFFLYSKLTVD
    KSRWQQGNVFSCSVMHEALH NHYTQKSLSLSPGK
```

---

A *Saccharomyces* alkaline phosphatase, Pho8, is produced as an inactive pro-enzyme. It is not GPI anchored, but is a transmembrane protein with its amino terminus extending out of a lysosome into the cytoplasm. Within the lysosome, an enzyme, PEP4, cleaves the carboxy terminus to activate the enzyme. Without wishing to be bound by theory, it is believed that mammalian alkaline phosphatases may also be generated as inactive pro-enzymes. This is because alkaline phosphatases can dephosphorylate ATP, so that activity in the ER could drain the ER of its major energy source. Without wishing to be bound by theory, it is believed embodiment, protease removal of the carboxy terminus reactivates the enzymatic activity of the alkaline phosphatase. In an embodiment, the pro-enzyme is more efficiently secreted than the enzyme without the carboxy terminus.

In some embodiments, for generation of the pro-enzyme, the native carboxy terminus of the alkaline phosphatase is replaced with the analogous sequence from hPLAP. In some embodiments, a mutation is made in the hydrophobic carboxy tail to promote protein secretion without cleavage of the carboxy terminus. In an illustrative embodiment, a single point mutation such as a substitution of leucine with e.g., arginine is generated in the hydrophobic carboxy terminus (e.g. ALLPLLAGTL is changed to e.g., ALLPLRAGTL) to result in secretion of the enzyme without removal of the carboxy terminus.

In an embodiment, the AP-based agent is altered to include a specific enzyme cleavage site which allows subsequent removal of the carboxy terminus. In an embodiment, the AP-based agent includes a protease cleavage site. Illustrative protease cleavage sites include, but are not limited to, cleavage sites recognized by furin, Rhinovirus 16 3C protease, factor Xa protease, trpysin, chymotrypsin, elastase, pepsin, papain subtilisin, thermolysin, V-8 protease, submaxillaris protease, clostripain, thrombin, collagenase, and any other endoproteases. In an alternative embodiment, the AP-based agent includes a cleavage site recognized by a digestive enzyme present in the GI tract. In such embodiments, the AP-based agent may be administered as a prodrug that is subsequently activated in the GI tract.

In an illustrative embodiment, the proenzyme is a proenzyme of bIAP IV having the following sequences:

based agent is optimized. The Kozak sequence is the nucleotide sequence flanking the ATG start codon that instructs the ribosome to start translation. There is flexibility in the design of a Kozak sequence, but one canonical sequence is GCCGCCACCATGG (SEQ ID NO: 37). The purine in the −3 position and the G in the +4 position are the most important bases for translation initiation. For hIAP, bIAP II, and bIAP IV, the second amino acid, that is, the one after the initiator methionine, is glutamine. Codons for glutamine all have a C in the first position. Thus, their Kozak sequences all have an ATGC sequence. Accordingly, in various embodiments, the ATGC sequence is changed to ATGG. This can be achieved by changing the second amino acid to a glycine, alanine, valine, aspartate, or glutamic acid, all of whose codons have a G in the first position. These amino acids may be compatible with signal peptide function. In alternative embodiments, the entire signal peptide is substituted for peptide having a canonical Kozak sequence and is derived from a highly expressed protein such as an immunoglobulin.

In various embodiments, the signal peptide of the AP-based agent may be deleted and/or substituted. For example,

```
BIAP IV with the hPLAP Carboxy Terminus and Mutation for Unprocessed
Secretion and RV3C Cleavage (at ...LEVLFQGP...): SEQ ID NO: 10
  1  mqwacvllll glwlqlsltf ipaeeedpaf wnrgaagald vakklqpiqt aaknvilflg 61  dgmgvptvta trilkgqmng klgpetplam dqfpyvalsk tynvdrqvpd sagtataylc 121  gvkgnyktig vsaaarynqc nttsgnevts vmnrakkagk svgvvttsry qhaspagaya 181  htvnrnwysd adlpadaqty gcqdiatqlv nnmdidvilg ggrmymfpeg tpdpeypydv 241  nqtgvrkdkr nlvqewqakh qgaqyvwnrt ellqaandps vthlmglfep admkynvqqd 301  ptkdptleem teaalqvlsr npqgfylfve ggridhghhe gkaymaltdt vmfdnaiaka 361  neltseldtl ilatadhshv fsfggytlrg tsifglapsk asdnksytsi lygngpgyvl 421  ggglrpdvnd sisedpsyrq qaavplsses hggedvavfa rgpqahlvhg vqeetfvahv 481  mafagcvepy tdcnlevlfq gpappagttd aahpgrsvvp allplragtl llletatap BIAP IV with hPLAP Carboxy Terminus and Mutation for Unprocessed
Secretion and FXa Cleavage (at ...IEGR...): SEQ ID NO: 11
  1  mqwacvllll glwlqlsltf ipaeeedpaf wnrgaagald vakklqpiqt aaknvilflg 61  dgmgvptvta trilkgqmng klgpetplam dqfpyvalsk tynvdrqvpd sagtataylc 121  gvkgnyktig vsaaarynqc nttsgnevts vmnrakkagk svgvvttsry qhaspagaya 181  htvnrnwysd adlpadaqty gcqdiatqlv nnmdidvilg ggrmymfpeg tpdpeypydv 241  nqtgvrkdkr nlvqewqakh qgaqyvwnrt ellqaandps vthlmglfep admkynvqqd 301  ptkdptleem teaalqvlsr npqgfylfve ggridhghhe gkaymaltdt vmfdnaiaka 361  neltseldtl ilatadhshv fsfggytlrg tsifglapsk asdnksytsi lygngpgyvl 421  ggglrpdvnd sisedpsyrq qaavplsses hggedvavfa rgpqahlvhg vqeetfvahv 481  mafagcvepy tdcnlappag ttdaahpieg rsvvpallpl ragtllllet atap
```

In various embodiments, the AP-based agent of the invention is efficiently expressed and secreted from a host cell. In an embodiment, the AP-based agent of the invention is efficiently transcribed in a host cell. In another embodiment, the AP-based agent exhibits enhanced RNA stability and/or transport in a host cell. In another embodiment, the AP-based agent is efficiently translated in a host cell. In another embodiment, the AP-based agent exhibits enhanced protein stability.

In various embodiments, the AP-based agents are efficiently expressed in a host cell. In an embodiment, the Kozak sequence of the DNA construct encoding the APthe signal peptide may be deleted, mutated, and/or substituted (e.g., with another signal peptide) to ensure optimal protein expression.

In some embodiments, The DNA construct encoding the AP-based agent of the invention comprises untranslated DNA sequences. Such sequences include an intron, which may be heterologous to the IAP protein or native to the IAP protein including the native first and/or second intron and/or a native 3' UTR. Without wishing to be bound by theory, it is believed that include of these sequences enhance protein expression by stabilizing the mRNA. Accordingly, in various embodiments, the DNA construct encoding the AP-based agent of the invention comprises the 5'UTR and/or the 3'UTR.

Provided below are illustrative IAP DNA sequences with a first intron and a 3'UTR:

hIAP with native first intron (shown as bolded and underlined)
SEQ ID NO: 12
ATGCAGGGGCCCTGGGTGCTGCTGCTGCTGGGCCTGAGGCTACAGCTCT
CCCTGGGCGTCATCCCAG**GTAATGAGGCTCCCCAAGCTGTTCCACACAC
AGGGCACCCCCTCAGCCAGGCTGACCTGATCTCTACTCTCCCCCTGGCC
AG**CTGAGGAGGAGAACCCGGCCTTCTGGAACCGCCAGGCAGCTGAGGCC
CTGGATGCTGCCAAGAAGCTGCAGCCCATCCAGAAGGTCGCCAAGAACC
TCATCCTCTTCCTGGGCGATGGGTTGGGGGTGCCCACGGTGACAGCCAC
CAGGATCCTAAAGGGGCAGAAGAATGGCAAACTGGGGCCTGAGACGCCC
CTGGCCATGGACCGCTTCCCATACCTGGCTCTGTCCAAGACATACAATG
TGGACAGACAGGTGCCAGACAGCGCAGCCACAGCCACGGCCTACCTGTG
CGGGGTCAAGGCCAACTTCCAGACCATCGGCTTGAGTGCAGCCGCCCGC
TTTAACCAGTGCAACACGACACGCGGCAATGAGGTCATCTCCGTGATGA
ACCGGGCCAAGCAAGCAGGAAAGTCAGTAGGAGTGGTGACCACCACACG
GGTGCAGCACGCCTCGCCAGCCGGCACCTACGCACACACAGTGAACCGC
AACTGGTACTCAGATGCTGACATGCCTGCCTCAGCCCGCCAGGAGGGGT
GCCAGGACATCGCCACTCAGCTCATCTCCAACATGGACATTGACGTGAT
CCTTGGCGGAGGCCGCAAGTACATGTTTCCCATGGGGACCCCAGACCCT
GAGTACCCAGCTGATGCCAGCCAGAATGGAATCAGGCTGGACGGGAAGA
ACCTGGTGCAGGAATGGCTGGCAAAGCACCAGGGTGCCTGGTATGTGTG
GAACCGCACTGAGCTCATGCAGGCGTCCCTGGACCAGTCTGTGACCCAT
CTCATGGGCCTCTTTGAGCCCGGAGACACGAAATATGAGATCCACCGAG
ACCCCACACTGGACCCCTCCCTGATGGAGATGACAGAGGCTGCCCTGCG
CCTGCTGAGCAGGAACCCCGCGGCTTCTACCTCTTTGTGGAGGGCGGC
CGCATCGACCATGGTCATCATGAGGGTGTGGCTTACCAGGCACTCACTG
AGGCGGTCATGTTCGACGACGCCATTGAGAGGGCGGGCCAGCTCACCAG
CGAGGAGGACACGCTGACCCTCGTCACCGCTGACCACTCCCATGTCTTC
TCCTTTGGTGGCTACACCTTGCGAGGGAGCTCCATCTTCGGGTTGGCCC
CCAGCAAGGCTCAGGACAGCAAAGCCTACACGTCCATCCTGTACGGCAA
TGGCCCCGGGCTACGTGTTCAACTCAGGCGTGCGACCAGACGTGAATGAG
AGCGAGAGCGGGAGCCCCGATTACCAGCAGCAGGCGGCGGTGCCCCTGT
CGTCCGAGACCCACGGAGGCGAAGACGTGGCGGTGTTTGCGCGCGGCCC
GCAGGCGCACCTGGTGCATGGTGTGCAGGAGCAGAGCTTCGTAGCGCAT
GTCATGGCCTTCGCTGCCTGTCTGGAGCCCTACACGGCCTGCGACCTGG
CGCCTCCCGCCTGCACCACCGACGCCGCGCACCCAGTTGCCGCGTCGCT
GCCACTGCTGGCCGGGACCCTGCTGCTGCTGGGGGCGTCCGCTGCTCCC
TGA hIAP with native 3' UTR (shown as bolded and underlined)
SEQ ID NO: 13
ATGCAGGGGCCCTGGGTGCTGCTGCTGCTGGGCCTGAGGCTACAGCTCT
CCCTGGGCGTCATCCCAGCTGAGGAGGAGAACCCGGCCTTCTGGAACCG
CCAGGCAGCTGAGGCCCTGGATGCTGCCAAGAAGCTGCAGCCCATCCAG
AAGGTCGCCAAGAACCTCATCCTCTTCCTGGGCGATGGGTTGGGGGTGC
CCACGGTGACAGCCACCAGGATCCTAAAGGGGCAGAAGAATGGCAAACT
GGGGCCTGAGACGCCCCTGGCCATGGACCGCTTCCCATACCTGGCTCTG
TCCAAGACATACAATGTGGACAGACAGGTGCCAGACAGCGCAGCCACAG
CCACGGCCTACCTGTGCGGGGTCAAGGCCAACTTCCAGACCATCGGCTT
GAGTGCAGCCGCCCGCTTTAACCAGTGCAACACGACACGCGGCAATGAG
GTCATCTCCGTGATGAACCGGGCCAAGCAAGCAGGAAAGTCAGTAGGAG
TGGTGACCACCACACGGGTGCAGCACGCCTCGCCAGCCGGCACCTACGC
ACACACAGTGAACCGCAACTGGTACTCAGATGCTGACATGCCTGCCTCA
GCCCGCCAGGAGGGGTGCCAGGACATCGCCACTCAGCTCATCTCCAACA
TGGACATTGACGTGATCCTTGGCGGAGGCCGCAAGTACATGTTTCCCAT
GGGGACCCCAGACCCTGAGTACCCAGCTGATGCCAGCCAGAATGGAATC
AGGCTGGACGGGAAGAACCTGGTGCAGGAATGGCTGGCAAAGCACCAGG
GTGCCTGGTATGTGTGGAACCGCACTGAGCTCATGCAGGCGTCCCTGGA
CCAGTCTGTGACCCATCTCATGGGCCTCTTTGAGCCCGGAGACACGAAA
TATGAGATCCACCGAGACCCCACACTGGACCCCTCCCTGATGGAGATGA
CAGAGGCTGCCCTGCGCCTGCTGAGCAGGAACCCCCGCGGCTTCTACCT
CTTTGTGGAGGGCGGCCGCATCGACCATGGTCATCATGAGGGTGTGGCT
TACCAGGCACTCACTGAGGCGGTCATGTTCGACGACGCCATTGAGAGGG
CGGGCCAGCTCACCAGCGAGGAGGACACGCTGACCCTCGTCACCGCTGA
CCACTCCCATGTCTTCTCCTTTGGTGGCTACACCTTGCGAGGGAGCTCC
ATCTTCGGGTTGGCCCCCAGCAAGGCTCAGGACAGCAAAGCCTACACGT
CCATCCTGTACGGCAATGGCCCGGGCTACGTGTTCAACTCAGGCGTGCG
ACCAGACGTGAATGAGAGCGAGAGCGGGAGCCCCGATTACCAGCAGCAG
GCGGCGGTGCCCCTGTCGTCCGAGACCCACGGAGGCGAAGACGTGGCGG
TGTTTGCGCGCGGCCCGCAGGCGCACCTGGTGCATGGTGTGCAGGAGCA
GAGCTTCGTAGCGCATGTCATGGCCTTCGCTGCCTGTCTGGAGCCCTAC
ACGGCCTGCGACCTGGCGCCTCCCGCCTGCACCACCGACGCCGCGCACC
CAGTTGCCGCGTCGCTGCCACTGCTGGCCGGGACCCTGCTGCTGCTGGG
GGCGTCCGCTGCTCCCTGA**TTTACTAAAACCTTGAAATAAAATTGTAAA
ACATCAGTTTGAAGGCCTGACTCTCAGGGTAGTTCTTTTTTAATTCTGG
GTTTT** bIAP IV with the first intron from bIAP I (shown as bolded and underlined)
SEQ ID NO: 14
ATGCAGTGGGCCTGTGTGCTGCTGCTGCTGGGCCTGTGGCTACAGCTCT
CCCTCACCTTCATCCCAGGTAATCAGGCGGCTCCCAGCAGCCCCTACTC

```
ACAGGGGCGGCTCTAGGCTGACCTGACCAACACTCTCCCCTTGGGCAGC
TGAGGAGGAAGACCCCGCCTTCTGGAACCGCCAGGCAGCCCAGGCCCTT
GATGTAGCCAAGAAGTTGCAGCCGATCCAGACAGCTGCCAAGAATGTCA
TCCTCTTCTTGGGGGATGGGATGGGGGTGCCTACGGTGACAGCCACTCG
GATCCTAAAGGGGCAGATGAATGGTAAGCTGGGACCTGAGACACCCCTG
GCCATGGACCAGTTCCCATACGTGGCTCTGTCCAAGACATACAACGTGG
ACAGACAGGTGCCAGACAGCGCAGGCACTGCCACTGCCTACCTGTGTGG
GGTCAAGGGCAACTACAAAACCATTGGTGTAAGTGCAGCCGCCCGCTAC
AACCAGTGCAACACAACAAGTGGCAATGAGGTCACGTCTGTGATGAACC
GGGCCAAGAAAGCAGGAAAGTCAGTGGGAGTGGTGACCACCTCCAGGGT
GCAGCATGCCTCCCCAGCCGGTGCTTATGCACACACGGTGAACCGAAAC
TGGTACTCAGATGCCGACCTGCCTGCCGATGCACAGACGTATGGCTGCC
AGGACATCGCCACACAACTGGTCAACAACATGGATATTGACGTGATCCT
GGGTGGAGGCCGAATGTACATGTTTCCTGAGGGGACCCCGGATCCTGAA
TACCCATACGATGTCAATCAGACTGGAGTCCGGAAGGACAAGCGGAATC
TGGTGCAGGAGTGGCAGGCCAAGCACCAGGGAGCCCAGTATGTGTGGAA
CCGCACGGAGCTCCTTCAGGCAGCCAATGACCCCAGTGTAACACACCTC
ATGGGCCTCTTTGAGCCGGCAGACATGAAGTATAATGTTCAGCAAGACC
CCACCAAGGACCCGACCCTGGAGGAGATGACGGAGGCGGCCCTGCAAGT
GCTGAGCAGGAACCCCAGGGCTTCTACCTCTTCGTGGAGGGAGGCCGC
ATTGACCACGGTCACCATGAAGGCAAAGCTTATATGGCACTGACTGATA
CAGTCATGTTTGACAATGCCATCGCCAAGGCTAACGAGCTCACTAGCGA
ACTGGACACGCTGATCCTTGCCACTGCAGACCACTCCCATGTCTTCTCT
TTTGGTGGCTACACACTGCGTGGGACCTCCATTTTCGGTCTGGCCCCA
GCAAGGCCTCAGACAACAAGTCCTACACCTCCATCCTCTATGGCAATGG
CCCTGGCTACGTGCTTGGTGGGGCTTAAGGCCCGATGTTAATGACAGC
ATAAGCGAGGACCCCTCGTACCGGCAGCAGGCGGCCGTGCCCCTGTCTA
GTGAGTCCACGGGGGCGAGGACGTGGCGGTGTTCGCGCGAGGCCCGCA
GGCGCACCTGGTGCACGGCGTGCAGGAGGAGACCTTCGTGGCGCACGTC
ATGGCCTTTGCGGGCTGCGTGGAGCCCTACACCGACTGCAATCTGCCGG
CCCCCTCTGGCCTCTCCGACGCCGCGCACCTGGCGGCCAGCCCGCCTTC
GCTGGCGCTGCTGGCCGGGGCGATGCTGCTGCTGCTGGCGCCTGCCTTG
TACTGA
```
bIAP IV with the 3' UTR from bIAP
(shown as bolded and underlined)
SEQ ID NO: 15
```
ATGCAGTGGGCCTGTGTGCTGCTGCTGCTGGGCCTGTGGCTACAGCTCT
CCCTCACCTTCATCCCAGCTGAGGAGGAAGACCCCGCCTTCTGGAACCG
CCAGGCAGCCCAGGCCCTTGATGTAGCCAAGAAGTTGCAGCCGATCCAG
ACAGCTGCCAAGAATGTCATCCTCTTCTTGGGGGATGGGATGGGGGTGC
CTACGGTGACAGCCACTCGGATCCTAAAGGGGCAGATGAATGGTAAGCT
GGGACCTGAGACACCCCTGGCCATGGACCAGTTCCCATACGTGGCTCTG
TCCAAGACATACAACGTGGACAGACAGGTGCCAGACAGCGCAGGCACTG
CCACTGCCTACCTGTGTGGGGTCAAGGGCAACTACAAAACCATTGGTGT
AAGTGCAGCCGCCCGCTACAACCAGTGCAACACAACAAGTGGCAATGAG
GTCACGTCTGTGATGAACCGGGCCAAGAAAGCAGGAAAGTCAGTGGGAG
TGGTGACCACCTCCAGGGTGCAGCATGCCTCCCCAGCCGGTGCTTATGC
ACACACGGTGAACCGAAACTGGTACTCAGATGCCGACCTGCCTGCCGAT
GCACAGACGTATGGCTGCCAGGACATCGCCACACAACTGGTCAACAACA
TGGATATTGACGTGATCCTGGGTGGAGGCCGAATGTACATGTTTCCTGA
GGGGACCCCGGATCCTGAATACCCATACGATGTCAATCAGACTGGAGTC
CGGAAGGACAAGCGGAATCTGGTGCAGGAGTGGCAGGCCAAGCACCAGG
GAGCCCAGTATGTGTGGAACCGCACGGAGCTCCTTCAGGCAGCCAATGA
CCCCAGTGTAACACACCTCATGGGCCTCTTTGAGCCGGCAGACATGAAG
TATAATGTTCAGCAAGACCCCACCAAGGACCCGACCCTGGAGGAGATGA
CGGAGGCGGCCCTGCAAGTGCTGAGCAGGAACCCCAGGGCTTCTACCT
CTTCGTGGAGGGAGGCCGCATTGACCACGGTCACCATGAAGGCAAAGCT
TATATGGCACTGACTGATACAGTCATGTTTGACAATGCCATCGCCAAGG
CTAACGAGCTCACTAGCGAACTGGACACGCTGATCCTTGCCACTGCAGA
CCACTCCCATGTCTTCTCTTTTGGTGGCTACACACTGCGTGGGACCTCC
ATTTTCGGTCTGGCCCCCAGCAAGGCCTCAGACAACAAGTCCTACACCT
CCATCCTCTATGGCAATGGCCCTGGCTACGTGCTTGGTGGGGCTTAAG
GCCCGATGTTAATGACAGCATAAGCGAGGACCCCTCGTACCGGCAGCAG
GCGGCCGTGCCCCTGTCTAGTGAGTCCCACGGGGGCGAGGACGTGGCGG
TGTTCGCGCGAGGCCCGCAGGCGCACCTGGTGCACGGCGTGCAGGAGGA
GACCTTCGTGGCGCACGTCATGGCCTTTGCGGGCTGCGTGGAGCCCTAC
ACCGACTGCAATCTGCCGGCCCCCTCTGGCCTCTCCGACGCCGCGCACC
TGGCGGCCAGCCCGCCTTCGCTGGCGCTGCTGGCCGGGGCGATGCTGCT
GCTGCTGGCGCCTGCCTTGTACTGA
```
**GGGGACCCGGGGGTGGGGACACAG
GCCCCGCCCTCCCTGGGAGGCAGGAAGCAGCTCTCAAATAAACTGTTCT
AAGTATGATACAGGAGTGATACATGTGTGAAGAGAAGCCCTTAGGTGGG
GGCACAGAGTGTCTGGGTGAGGGGGGTCAGGGTCACATCAGGAGGTTAG
GGAGGGGTTGATGAAGGGCTGACGTTGAGCAAAGACCAAAGGCAACTCA
GAAGGACAGTGGTGCAGGACTGGGTGTGGTCAGCAGGGGACTGGTTGG
GGGATCC**

In various embodiments, the present invention contemplates the use of bacterial alkaline phosphatases. In some embodiments, the AP-based agent of the invention is derived from *Bacillus subtilis*. *Bacillus subtilis* is a Gram-positive bacterium found in soil and the GI tract of humans. *Bacillus subtilis* secretes high levels of proteins into the environment and in the human GI tract that are properly folded. Without wishing to be bound by theory, it is believed that *Bacillus subtilis* secreted proteins in the GI tract may be resistant to degradation by common GI proteases. *Bacillus subtilis* expresses at high levels an alkaline phosphatase multigene family. Among those isozymes, alkaline phosphatase IV is responsible for the majority of total alkaline phosphatase expression and activity in *B. subtilis*. In some embodiments, the AP-based agent of the invention is derived from *Bacillus licheniformis*. In some embodiments, the AP-based agent of the invention is derived from *Escherichia coli*.

Accordingly, in an illustrative embodiment, the AP-based agent of the invention is derived from alkaline phosphatase IV of *Bacillus subtilis*. In an embodiment, the bacterial alkaline phosphatase may have the following nucleotide and amino acid sequences:

*Bacillus subtilis* JH642 alkaline phosphatase IV, mature protein nucleotide sequence
SEQ ID NO: 16
AAAAAACAAGACAAAGCTGAGATCAGAAATGTCATTGTGATGATAGGCG

ACGGCATGGGGACGCCTTACATAAGAGCCTACCGTTCCATGAAAAATAA

CGGTGACACACCGAATAACCCGAAGTTAACAGAATTTGACCGGAACCTG

ACAGGCATGATGATGACGCATCCGGATGACCCTGACTATAATATTACAG

ATTCAGCAGCAGCCGGAACAGCATTAGCGACAGGCGTTAAGACATATAA

CAATGCAATTGGCGTCGATAAAAACGGAAAAAAAGTGAAATCTGTACTT

GAAGAGGCCAAACAGCAAGGCAAGTCAACAGGGCTTGTCGCCACGTCTG

AAATTAACCACGCCACTCCAGCCGCATATGGCGCCCACAATGAATCACG

GAAAAACATGGACCAAATCGCCAACAGCTATATGGATGACAAGATAAAA

GGCAAACATAAAATAGACGTGCTGCTCGGCGGCGGAAAATCTTATTTTA

ACCGCAAGAACAGAAACTTGACAAAGGAATTCAAACAAGCCGGCTACAG

CTATGTGACAACTAAACAAGCATTGAAAAAAAATAAAGATCAGCAGGTG

CTCGGGCTTTTCGCAGATGGAGGGCTTGCTAAAGCGCTCGACCGTGACA

GTAAAACACCGTCTCTCAAAGACATGACGGTTTCAGCAATTGATCGCCT

GAACCAAAATAAAAAAGGATTTTTCTTGATGGTCGAAGGGAGCCAGATT

GACTGGGCGGCCCATGACAATGATACAGTAGGAGCCATGAGCGAGGTTA

AAGATTTTGAACAGGCCTATAAAGCCGCGATTGAATTTGCGAAAAAAGA

CAAACATACACTTGTGATTGCAACTGCTGACCATACAACCGGCGGCTTT

ACCATTGGCGCAAACGGGGAAAAGAATTGGCACGCAGAACCGATTCTCT

CCGCTAAGAAAACACCTGAATTCATGGCCAAAAAAATCAGTGAAGGCAA

GCCGGTTAAAGATGTGCTCGCCCGCTATGCCAATCTGAAAGTCACATCT

GAAGAAATCAAAAGCGTTGAAGCAGCTGCACAGGCTGACAAAAGCAAAG

GGGCCTCCAAAGCCATCATCAAGATTTTTAATACCCGCTCCAACAGCGG

ATGGACGAGTACCGATCATACCGGCGAAGAAGTACCGGTATACGCGTAC

GGCCCCGGAAAAGAAAAATTCCGCGGATTGATTAACAATACGGACCAGG

CAAACATCATATTTAAGATTTTAAAAACTGGAAAA

*Bacillus subtilis* JH642 alkaline phosphatase IV, mature protein amino acid sequence
SEQ ID NO: 17
KKQDKAEIRNVIVMIGDGMGTPYIRAYRSMKNNGDTPNNPKLTEFDRNL

TGMMMTHPDDPDYNITDSAAAGTALATGVKTYNNAIGVDKNGKKVKSVL

EEAKQQGKSTGLVATSEINHATPAAYGAHNESRKNMDQIANSYMDDKIK

GKHKIDVLLGGGKSYFNRKNRNLTKEFKQAGYSYVTTKQALKKNKDQQV

LGLFADGGLAKALDRDSKTPSLKDMTVSAIDRLNQNKKGFELMVEGSQI

DWAAHDNDTVGAMSEVKDFEQAYKAAIEFAKKDKHTLVIATADHTTGGF

TIGANGEKNWHAEPILSAKKTPEFMAKKISEGKPVKDVLARYANLKVTS

EEIKSVEAAAQADKSKGASKAIIKIENTRSNSGWTSTDHTGEEVPVYAY

GPGKEKFRGLINNTDQANIIFKILKTGK

In some embodiments, the AP-based agents include bacterial alkaline phosphatases that have one or more mutations that alter catalytic activity. In some embodiments, the bacterial alkaline phosphatases include one or more mutations such that their catalytic activity is similar or higher than mammalian alkaline phosphatases. In some embodiments, the bacterial alkaline phosphatases include one or more mutations that alter their de-phosphorylation profile. In an embodiment, the bacterial alkaline phosphatases of the invention exhibits similar de-phosphorylation profile as mammalian alkaline phosphatases. In some embodiments, the bacterial alkaline phosphatases include one or more mutations that alter their activity at higher pH. In an embodiment, the bacterial alkaline phosphatases of the invention exhibits similar activity at higher pH as mammalian alkaline phosphatases. In some embodiments, the bacterial alkaline phosphatases include one or more mutations that alter their metal requirements. In an embodiment, the bacterial alkaline phosphatases of the invention exhibit metal requirements (e.g., Mg) similar to mammalian alkaline phosphatases.

For example, in certain embodiments, the AP-based agent of the invention is derived from *Bacillus subtilis* JH642 alkaline phosphatase IV, and has one or more mutations at positions 101, 328, A330, and 374. For example, the AP-based agent may include one or more of the following mutations: D101A, W328H, A330N and G374C.

In various embodiments, the AP-based agent of the invention comprises a nucleotide sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In some embodiments, the AP-based agent of the invention comprises an amino sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In various embodiments, the AP-based agent of the invention may comprise an amino acid sequence having one or more amino acid mutations relative any of the protein sequences described herein. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and 5-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general).

Mutations may also be made to the nucleotide sequences of the alkaline phosphatases by reference to the genetic code, including taking into account codon degeneracy. In various embodiments, the DNA construct encoding the AP-based agent is codon optimized for optimal protein expression in a host cell.

Mutations may be made to the AP-based agent of the invention to select for agents with desired characteristics. For examples, mutations may be made to generate AP-based agents with enhanced catalytic activity or protein stability. In various embodiments, directed evolution may be utilized to generate AP-based agents of the invention. For example, error-prone PCR and DNA shuffling may be used to identify mutations in the bacterial alkaline phosphatases that confer enhanced activity.

In various embodiments, the AP-based agent of the invention possesses desirable characteristics, including, for example, high specific activity. In various embodiments, the alkaline phosphatase of the invention possesses a specific activity of at least about 100 U/mg to about 20,000 U/mg. In various embodiments, the alkaline phosphatase of the invention possesses a specific activity of at least about 100 U/mg, about 200 U/mg, about 300 U/mg, about 400 U/mg, about 500 U/mg, about 600 U/mg, about 700 U/mg, about 800 U/mg, about 900 U/mg, about 1,000 U/mg, about 2,000 U/mg, about 3,000 U/mg, about 4,000 U/mg, about 5,000 U/mg, about 6,000 U/mg, about 7,000 U/mg, about 8,000 U/mg, about 9,000 U/mg, about 10,000 U/mg, about 11,000 U/mg, about 12,000 U/mg, about 13,000 U/mg, about 14,000 U/mg, about 15,000 U/mg, about 16,000 U/mg, about 17,000 U/mg, about 18,000 U/mg, about 19,000 U/mg, or about 20,000 U/mg.

In various embodiments, the formulation is resistant to compression and therefore suitable for tableting.

In various embodiments, the AP-based agent of the invention is stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the alkaline phosphatase is stable in the large intestine, optionally selected from one or more of colon transversum, colon descendens, colon ascendens, colon sigmoidenum and cecum. In a specific embodiment, the alkaline phosphatase is stable in the small intestine, optionally selected from one or more of duodenum, jejunum, and ileum. In some embodiments, the alkaline phosphatase is resistant to proteases in the GI tract, including for example, the small intestine. In some embodiments, the alkaline phosphatase is substantially active at a pH of about 5.0 or above. For example, the alkaline phosphatase may be substantially active at a pH of about 6.0 to about 12, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 8.0, or about 8.5, or about 9.0, or about 9.5, or about 10.0, or about 10.5, or about 11.0, or about 11.5, or about 12.0 (including, for example, via formulation, as described herein). In some embodiments, stable refers to an enzyme that has a long enough half-life and maintains sufficient activity for therapeutic effectiveness.

In various embodiments, the AP-based agent of the invention is stable in chyme.

In some embodiments, the AP-based agent described herein includes derivatives that are modified, i.e., by the covalent attachment of any type of molecule to the alkaline phosphatase such that covalent attachment does not prevent the activity of the enzyme. For example, but not by way of limitation, derivatives include alkaline phosphatases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids. In various embodiments, the AP-based agent is glycosylated to ensure proper protein folding.

In still other embodiments, the AP-based agents of the invention may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The AP-based agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the alkaline phosphatases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Further, any AP-based agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, malt, rice, flour, chalk, silica gel, sodium stearate, glycerol monostearate, talc, sodium chloride, dried skim milk, glycerol, propylene, glycol, povidone, crospovidone, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the AP-based agent and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Methods of Making the APs of the Invention

The IAPs of the invention are made using standard molecular biology techniques. For example, nucleic acid compositions encoding the IAPs of the invention are also provided, as well as expression vectors containing the nucleic acids and host cells transformed with the nucleic acid and/or expression vector compositions. As will be appreciated by those in the art, the protein sequences depicted herein can be encoded by any number of possible nucleic acid sequences, due to the degeneracy of the genetic code.

As is known in the art, the nucleic acids encoding the components of the invention can be incorporated into expression vectors as is known in the art, and depending on the host cells, used to produce the IAP compositions of the invention. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

The IAPs of the invention are made by culturing host cells comprising the expression vector(s) as is well known in the art. Once produced, traditional purification steps are done.

Formulations

The present invention provides the described AP-based agent and/or pharmaceutical compositions (and/or additional therapeutic agents) in various formulations. Any AP-based agent and/or pharmaceutical composition (and/or additional therapeutic agents) described herein can take the form of tablets, pills, pellets, capsules, capsules containing liquids, capsules containing multiparticulates, powders, solutions, emulsion, drops, suppositories, emulsions, aerosols, sprays, suspensions, delayed-release formulations, sustained-release formulations, controlled-release formulations, or any other form suitable for use.

The formulations comprising the AP-based agent and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. For example, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting).

In one embodiment, the AP-based agent (and/or additional therapeutic agents) described herein is formulated as a composition adapted for a mode of administration described herein In various embodiments, the administration the AP-based agent and/or pharmaceutical compositions (and/or additional therapeutic agents) is any one of oral, intravenous, and parenteral. For example, routes of administration include, but are not limited to, oral, intradermal, intramuscular, intraperitoneal, intravenous, subcutaneous, intranasal, epidural, sublingual, intranasal, intracerebral, intravaginal, transdermal, rectally, by inhalation, or topically (e.g., to the ears, nose, eyes, or skin).

In one embodiment, the AP-based agent and/or pharmaceutical compositions (and/or additional therapeutic agents) described herein are formulated as compositions adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any alkaline phosphatase (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the AP-based agent and/or pharmaceutical compositions (and/or additional therapeutic agent) are formulated as solid dosage forms such as tablets, dispersible powders, granules, and capsules. In one embodiment, the AP-based agent and/or pharmaceutical compositions (and/or additional therapeutic agent) are formulated as a capsule. In another embodiment, the AP-based agent and/or pharmaceutical compositions (and/or additional therapeutic agent) are formulated as a tablet. In yet another embodiment, the AP-based agent and/or pharmaceutical compositions (and/or additional therapeutic agent) are formulated as a soft-gel capsule. In a further embodiment, the AP-based agent and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

In various embodiments, the formulations of the AP-based agents may additionally comprise a pharmaceutically acceptable carrier or excipient. As one skilled in the art will recognize, the formulations can be in any suitable form appropriate for the desired use and route of administration.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

The formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The formulation can also include one or more application solvents. Some of the more common solvents that can be used to apply, for example, a delayed-release coating composition include isopropyl alcohol, acetone, methylene chloride and the like.

The formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from antacid materials such as aluminum hydroxides, calcium hydroxides, magnesium hydroxides and magnesium oxide.

In various embodiments, the formulation can additionally include magnesium and/or zinc. Without wishing to be bound by theory, the inclusion of magnesium and/or zinc in the formulation promotes protein folding (e.g., dimer formation) and bioactivity of the AP-based agent. In some embodiments, the formulation can include magnesium at a concentration of from about 1 µM to greater than 500 mM (e.g., from about 1 µM to more than 5 mM), inclusive of all ranges and values therebetween. In an embodiment, the magnesium is present in the formulation at 1.0 mM. In some embodiments, the formulation can include zinc at a concentration of about 1 µM to greater than 100 mM (e.g., from about 1 µM to more than 1 mM), inclusive of all ranges and values therebetween. In an embodiment, the zinc is present in the formulation at 0.1 mM. In various embodiments, the formulation of the present invention is substantially free of metal chelators.

In various embodiments, the pH of the formulation ensures that the AP-based agent is properly folded (e.g., dimer formation) and is bioactive. In some embodiments, the formulation is maintained at a pH such that the amino acids which coordinate the binding of magnesium and/or zinc within the AP-based agent are not protonated. Protonation of such coordinating amino acids may lead to loss of metal ions and bioactivity and dimer disassociation. In various embodiments, the pH of the formulation is greater than about 6, about 6.5, about 7, about 7.5, about 8, about 8.5, about 9, about 9.5, about 10, about 10.5, about 11, about 11.5, or about 12.

Besides inert diluents, the oral compositions can also include adjuvants such as sweetening, flavoring, and perfuming agents.

In various embodiments, the AP-based agent and/or pharmaceutical compositions (and/or additional therapeutic agents) are formulated for systemic or local delivery. In an embodiment, administration is systemic. In another embodiment, it may be desirable to administer locally to the area in need of treatment.

Various methods may be used to formulate and/or deliver the agents described herein to a location of interest. For example, the alkaline phosphatase and/or pharmaceutical compositions (and/or additional therapeutic agents) described herein may be formulated for delivery to the GI tract. The GI tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the alkaline phosphatases and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the alkaline phosphatases and/or pharmaceutical compositions (and/or additional therapeutic agents) may be administered to a subject, by, for example, directly or indirectly contacting the mucosal tissues of the GI tract.

In various embodiments, the administration of the AP-based agent and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), direct infusion (e.g., duodenal infusion), endoscopy, colonoscopy, or enema.

For example, in various embodiments, the present invention provides modified release formulations comprising at least one AP-based agent (and/or additional therapeutic agents), wherein the formulation releases a substantial amount of the AP-based agent (and/or additional therapeutic agents) into one or more regions of the GI tract. For example, the formulation may release at least about 60% of the AP-based agent after the stomach and into one or more regions of the GI tract.

In various embodiments, the modified-release formulation of the present invention releases at least 60% of the AP-based agent (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the intestines.

In various embodiments, the modified-release formulation of the present invention releases at least 60% of the AP-based agent (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the small intestine (e.g., one or more of duodenum, jejunum, ileum, and ileocecal junction).

In various embodiments, the modified-release formulation of the present invention releases at least 60% of the AP-based agent (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the large intestine (e.g., one or more of cecum, ascending, transverse, descending or sigmoid portions of the colon, and rectum).

In various embodiments, the modified-release formulation does not substantially release the AP-based agent (or additional therapeutic agents) in the stomach.

In certain embodiments, the modified-release formulation releases the AP-based agent (or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation does not substantially release in the stomach. In these embodiments, the modified-release formulation substantially releases in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation substantially releases in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the alkaline phosphatase and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the alkaline phosphatase and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total alkaline phosphatase and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the alkaline phosphatase and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the alkaline phosphatase and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of alkaline phosphatase and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulation of the invention is substantially stable in chyme. For example, there is, in some embodiments, a loss of less about 50% or about 40%, or about 30%, or about 20%, or about 10% of AP-based agent activity in about 10, or 9, or 8, or 7, or 6, or 5, or 4, or 3, or 2, or 1 hour from administration.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the GI tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient (s) until it reaches the small intestine or large intestine.

In various embodiments, the present powder formulations (e.g. AP-based agent as a powder) is coated to provide protection of the active agent in the GI tract, including the stomach. For example, in some embodiments, the present powder formulations can be encapsulated in an enterically-coated capsule. Additionally, in some embodiments, the powder formulations (e.g. AP-based agent as a powder) itself is coated with one or more coatings, e.g. one or more modified-release coatings as described herein (e.g. after a step of granulating the powder). Further, in some embodiments, the present powder formulations (e.g. AP-based agent as a powder) can be compressed into a tablet that is coated.

In various embodiments, the modified-release formulation of the present invention may utilize one or more modified-release coatings such as delayed-release coatings to provide for effective, delayed yet substantial delivery of the alkaline phosphatase to the GI tract together with, optionally, additional therapeutic agents.

In various embodiments, the modified-release formulation of the present invention may utilize one or more modified-release coatings such as delayed-release coatings to provide for effective, delayed yet substantial delivery of the alkaline phosphatase to the intestines together with, optionally, other additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In an embodiment, the delayed-release coating includes the enteric agent EUDRAGIT® L 100.

By way of non-limiting example, there are various EUDRAGIT® formulations that dissolve at rising pH, with formulations that dissolve at pH>5.5 (EUDRAGIT® L30 D-550), pH>6.0 (EUDRAGIT® L12, 5), and pH>7.0 (EUDRAGIT® FS 30D). Since the ileum has the highest pH in the small intestine, ranging from 7.3 to 7.8, the use of EUDRAGIT® FS 30D as an enteric agent, may delay dissolution until the ileum thereby localizing the release of the AP-based agent to the ileum. However, the jejunum has a pH ranging from 6.6 to 7.4, therefore, the release may initiate in some patients in the jejunum, if the pH is at 7.0 or above. In such embodiments, the AP-based agent may be delivered with an antibiotic/inhibitor combination as described. The different types of EUDRAGIT® can be combined with each other, or multiple different types of EUDRAGIT® coatings can be combined to fine tune the dissolution profile to achieve targeted delivery to achieve optimal function. For example, EUDRAGIT® L100, EUDRAGIT® S100, and triethyl citrate may be mixed together at a ratio of, for example, about 72.7/18.2/9.1, to form a coating that substantially releases at a pH of greater than about 6.2. In another example, EUDRAGIT® L100, EUDRAGIT® S100, and triethyl citrate may be mixed together at a ratio of, for example, about 30/60.9/9, to form a coating that substantially releases at a pH of greater than about 6.7. In a further example, DuoCoat™ (Kuecept, Ltd.) may be used that uses two coatings of enteric polymers (like EUDRAGIT®), an outer layer, and an inner layer of partially neutralized enteric polymer and a buffer agent. The DuoCoat™ technology allows more rapid release of the therapeutic agent initiated at the targeted pH compared to a single coating of the enteric polymer (Liu et al., 2010, European J. Pharmaceutics and Biopharmaceuticals 47:311, the entire contents of all of which are incorporated herein by reference). Release was demonstrated to be targeted to the ileum and/or ileoceacal junction in 10 healthy volunteers (Varum et al., 2013, European J. Pharmaceutics and Biopharmaceuticals 84:573, the entire contents of all of which are incorporated herein by reference).

In certain embodiments, one or more coating system additives are used with the enteric agent. For example, one or more PlasACRYL™ additives may be used as an antitacking agent coating additive. Illustrative PlasACRYL™ additives include, but are not limited to PlasACRYL™ HTP20 and PlasACRYL™ T20.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000) or pectin. In an embodiment, the present invention contemplates the use of a delayed-release coating that degrade as a function of time which comprises a swell layer comprising croscarmellos sodium and hydroxypropylcellulose. In such embodiment, the formulation may further include an osmotic rupture coating that comprises ethylcellulose such as ethylcellulose dispersions.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora. For example, in various embodiments, the delayed-release coating may be degraded by a microbial enzyme present in the gut flora. In an embodiment, the delayed-release coating may be degraded by a bacteria present in the small intestine. In another embodiment, the delayed-release coating may be degraded by a bacteria present in the large intestine.

In various embodiments, the modified release formulation is designed for release in the colon. Various colon-specific delivery approaches may be utilized. For example, the modified release formulation may be formulated using a colon-specific drug delivery system (CODES) as described for example, in Li et al., *AAPS PharmSciTech* (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT® E), the outer coating is enteric, along with a hydroxypropyl methylcellulose barrier layer interposed in between. In another embodiment, colon delivery may be achieved by formulating the alkaline phosphatase (and/or additional therapeutic agent) with specific polymers that degrade in the colon such as, for example, pectin. The pectin may be further gelled or cross-linked with a cation such as a zinc cation. In an embodiment, the formulation is in the form of ionically crosslinked pectin beads which are further coated with a polymer (e.g., EUDRAGIT® polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of the AP-based agent (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulations provide for substantial uniform dissolution of the AP-based agent (and/or additional therapeutic agent) in the area of release in the GI tract. In an embodiment, the present formulation minimizes patchy or heterogeneous release of the AP-based agent.

In various embodiments, the present invention provides for modified-release formulations that release multiple doses of the AP-based agent, at different locations along the intestines, at different times, and/or at different pH. In an illustrative embodiment, the modified-release formulation comprises a first dose of the AP-based agent and a second dose of the AP-based agent, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the AP-based agent at different locations along the intestines, at different times, and/or at different pH.

In various embodiments, the invention provides a formulation comprising: a core particle having a base coat comprising one or more AP-based agents, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more AP-based agents may further comprise one or more additional therapeutic agents.

Optionally a plurality of base coats may be applied to the core particle each of which may contain an AP-based agent and/or an additional therapeutic agent. In an embodiment, the core particle includes sucrose. In an embodiment, an AP-based agent can be sprayed onto an inert core (e.g., a sucrose core) and spray-dried with an enteric layer to form pellets or beads containing AP-based agents.

Optionally, the core particle may comprise one or more AP-based agents and/or one or more additional therapeutic agents. In one embodiment, one or more doses of the AP-based agent may be encapsulated in a core particle, for example, in the form of a microsphere or a mini-sphere. For example, the AP-based agent may be combined with a polymer (e.g., latex), and then formed into a particulate, micro-encapsulated enzyme preparation, without using a sucrose core. The microspheres or mini-spheres thus formed may be optionally covered with a delayed-release coating.

A variety of approaches for generating particulates (such as microspheres, mini-spheres, aggregates, other) may be utilized for the inclusion of enzymatic proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form, for example, microspheres or mini-spheres. Alternatively, the alkaline phosphatase and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzymatic protein, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment. In an embodiment, alkaline phosphatase may be initially solubilized as an emulsion, microemulsion, or suspension and then formulated into solid mini-spheres or microspheres. The formulation may then be coated with, for example, a delayed-release, sustained-release, or controlled-release coating to achieve delivery at a specific location such as, for example, the intestines.

In various embodiments, the formulation may comprise a plurality of modified-release particles or beads or pellets or microspheres. In an embodiment, the formulation is in the form of capsules comprising multiple beads. In another embodiment, the formulation is in the form of capsules comprising multiple pellets. In another embodiment, the formulation is in the form of capsules comprising multiple microspheres or mini-spheres.

In some embodiments, before applying the delayed-release coating to the coated core particle, the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, sodium stearyl fumarate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In various embodiments, the formulations of the present invention take the form of those as described in International Patent Application No. PCT/US15/54606, the entire contents of all of which are incorporated herein by reference.

In various embodiments, the formulations of the present invention take the form of those as described in one or more of U.S. Pat. Nos. 8,535,713 and 8,9117,77 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those as described in International Patent Publication No. WO 2008/135090, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290, the contents of which are hereby incorporated by reference in their entirety.

In various embodiments, the process of formulating the AP-based agent is sufficiently gentle such that the tertiary structure of the AP-based agent (e.g., dimeric structure) is substantially intact. In various embodiments, the process of formulating the AP-based agent includes a step of refolding the AP-based agent. In such embodiments, the step of refolding the AP-based agent may include the addition of magnesium and/or cyclodextrin.

In various embodiments, the modified-release formulation is a modified release powder formulation.

In various embodiments, the modified-release formulation including AP-based agents described herein, and variants thereof) and/or additional therapeutic agents is administered orally.

Suitable dosage forms for oral use include, for example, solid dosage forms such as tablets, capsules, powders, and granules. In various embodiments, the modified-release formulation is in the form of powders. In some embodiments, the powdered formulations of the present invention can be added to food (e.g. juices, strained and/or pureed foods (e.g. fruits, vegetables), sauces, infant formulas, milk, etc.). In various embodiments, the modified-release formulation is in the form of a sachet. In various embodiments, the modified-release formulation is in the form of tablets. In an embodiment, the modified-release formulation is in the form of tablets comprising powders. In various embodiments, the modified-release formulation is in the form of capsules. In an embodiment, the modified-release formulation is in the form of capsules comprising powders.

In various embodiments, the modified-release formulation of the invention is in the form of powders. In various embodiments, the powders are formed by spray drying and/or by spray-dried dispersion (SDD) technology. In some embodiments, the powders comprising AP-based agents are formed by dissolving AP-based agents and polymers in a solvent and then spray-drying the solution. The resulting powder comprises the AP-based agents dispersed within a solid polymeric matrix.

Various types of polymers may be used for the modified-release formulation of the invention. In some embodiments, the polymer is an enteric polymer that is substantially stable in acidic environments and substantially unstable in near neutral to alkaline environments. In an embodiment, the enteric polymer is substantially stable in gastric fluid.

Exemplary polymers include, but are not limited to, copovidone, polyvinyl caprolactam-polyvinyl acetate-polyethyleneglycol copolymer, poly(vinylpyrrolidinone) (PVP), hydroxypropylmethylcellulose or hypromellose (HPMC), hypromellose phthalate (HPMCP), hypromellose acetate succinate (HPMCAS), methacrylate/methacrylic acid copolymer, and mixtures thereof. In an embodiment, the polymer is HPMCAS. In various embodiments, the polymer is HPMCAS LF, LG, MF, MG, HF, or HG. In an embodiment, the polymer is HPMCAS HF.

Various types of solvents/buffers may be used for preparation of the powders of the invention. In an embodiment, the solvents/buffers are organic solvents/buffers. Exemplary solvents/buffers that may be used to dissolve the AP-based agent and polymer prior to spray-drying include, but are not limited to, ethanol, methanol, acetone, IPA, tetrahydrafuran, dichloromethane, and mixtures thereof. In various embodiments, the solvent used is water such as distilled DI water. In various embodiments, the buffer used is monosodium phosphate monohydrate.

In some embodiments, enzyme co-factors including zinc and magnesium are used. In an embodiment, the enzyme co-factor zinc is used. In an embodiment, the zinc is provided as zinc sulfate heptahydrate. In another embodiment, the enzyme co-factor magnesium is used. In an embodiment, the magnesium is provided as magnesium sulfate heptahydrate.

In some embodiments, the formulation includes a protein stabilizer such as trehalose, mannitol, Tween 80, or polyvinyl alcohol. In an embodiment, the stabilizer is trehalose.

In some embodiments, surfactants may be included for the preparation of the powders of the invention. The surfactants may be used as solubilizers or emulsifying agents. Exemplary surfactants include, but are not limited to, vitamin E polyethylene glycol succinate, sorbitan monostearate—60/80, polysorbate 20, polysorbate 80, and polyoxyl 40 hydrogenated castor oil.

In various embodiments, the powders comprising AP-based agents becomes a gel at a pH of about 1-5 (e.g., a pH of about 1, about 2, about 3, about 4, or about 5). In various embodiments, the powders comprising AP-based agent becomes a gel in the presence of stomach acid. In such embodiments, the powders do not substantially release the AP-based agent upon forming a gel in the stomach. In various embodiments, the AP-based agent is released from the gel after passing from the stomach. In various embodiments, the AP-based agent is released from the gel into one or more regions of the intestines. In various embodiments, at pH values greater than about 5 (e.g. about 5, or 6, or 7, or 8, or 9) the gel transforms back into the solution phase and releases the beta-lactamase enzyme.

In various embodiments, the formulation of the present invention is in the form of powders comprising the AP-based agent dispersed within a solid polymeric matrix. In some embodiments, the powders are formed by dissolving AP-based agent and polymers in a solvent to form a solution that is subsequently spray-dried. In various embodiments, the solution for spray-drying comprises about 0.1-1% by weight of AP-based agent. For example, the AP-based agent may be present about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1.0% by weight. In some embodiments, the solution comprises about 1-10% by weight a polymer (e.g., HPMCAS-HF). For example, the polymer may be present at about 1%, about 2%, about 3%, about 4%, about 5%, about 6%, about 7%, about 8%, about 9%, or about 10% by weight. In some embodiment, the solution comprises about 0.05-0.5% by weight buffer (e.g., monosodium phosphate monohydrate). For example, the buffer may be present at about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.25%, about 0.30%, about 0.35%, about 0.40%, about 0.45%, or about 0.50% by weight. In some embodiment, the solution comprises about 0.001-0.01% by weight zinc (e.g., zinc sulfate heptahydrate). For example, the zinc may be present at about 0.001%, about 0.002%, about 0.003%, about 0.004%, about 0.005%, about 0.006%, about 0.007%, about 0.008%, about 0.009%, or about 0.01% by weight. In some embodiment, the solution comprises about 0.01-0.1% by weight magnesium (e.g., magnesium sulfate heptahydrate). For example, the magnesium may be present at about 0.01%, about 0.02%, about 0.03%, about 0.04%, about 0.05%, about 0.06%, about 0.07%, about 0.08%, about 0.09%, or about 0.1% by weight. In some embodiment, the solution comprises about 0.1-1% by weight a protein stabilizer (e.g., trehalose). For example, the protein stabilizer may be present at about 0.1%, about 0.2%, about 0.3%, about 0.4%, about 0.5%, about 0.6%, about 0.7%, about 0.8%, about 0.9%, or about 1% by weight. In some embodiments, the solution comprises about 90-99.9% by weight solvent (e.g., water). For example, the solvent may be present at about 90%, about 91%, about 92%, about 93%, about 94%, about 95%, about 96%, about 97%, about 98%, or about 99% by weight.

In some embodiments, the solution for spray drying comprises about 0.3% by weight by weight of the AP-based agent; about 4% by weight of the polymer (e.g., HPMCAS-HF); about 0.1% by weight of the buffer (e.g., monosodium phosphate monohydrate); about 0.003% by weight of the zinc (e.g., zinc sulfate heptahydrate); about 0.03% by weight of the magnesium (e.g., magnesium sulfate heptahydrate); about 0.3% by weight the protein stabilizer (e.g., trehalose), and about 95% by weight the solvent (e.g., water).

In some embodiments, the solution for spray drying comprises about 0.25% by weight by weight of the AP-based agent; about 4.372% by weight of the polymer (e.g., HPMCAS-HF); about 0.1% by weight of the buffer (e.g., monosodium phosphate monohydrate); about 0.003% by weight of the zinc (e.g., zinc sulfate heptahydrate); about 0.025% by weight of the magnesium (e.g., magnesium sulfate heptahydrate); about 0.25% by weight the protein stabilizer (e.g., trehalose), and about 95% by weight the solvent (e.g., water).

Powders are formed following spray-drying (for example, by spray-dried dispersion technology) of the solution described herein. In various embodiments, the powders of the invention comprise about 1-10% by weight of AP-based agent. For example, the AP-based agent may be present about 1%, about 2%, about 3%, about 4%, about 5%, 6%, about 7%, about 8%, about 9%, or about 10% by weight. In some embodiments, the solution comprises about 80-95% by weight a polymer (e.g., HPMCAS-HF). For example, the polymer may be present at about 80%, about 81%, about 82%, about 83%, about 84%, about 85%, about 86%, about 87%, about 88%, about 89%, about 90%, about 91%, about 92%, about 93%, about 94%, or about 95% by weight. In some embodiment, the solution comprises about 1-10% by weight buffer (e.g., monosodium phosphate monohydrate). For example, the buffer may be present at about 1%, about 2%, about 3%, about 4%, about 5%, 6%, about 7%, about 8%, about 9%, or about 10% by weight. In some embodiment, the solution comprises about 0.01-0.1% by weight zinc (e.g., zinc sulfate heptahydrate). For example, the zinc may be present at about 0.01%, about 0.02%, about 0.03%, about 0.04%, about 0.05%, about 0.06%, about 0.07%, about 0.08%, about 0.09%, or about 0.1% by weight. In some embodiment, the solution comprises about 0.1-1% by weight magnesium (e.g., magnesium sulfate heptahydrate). For example, the magnesium may be present at about 0.1%, about 0.2%, about 0.3%, about 0.4%, about 0.5%, about 0.6%, about 0.7%, about 0.8%, about 0.9%, or about 1% by weight. In some embodiment, the solution comprises about 1-10% by weight a protein stabilizer (e.g., trehalose). For example, the protein stabilizer may be present at about 1%, about 2%, about 3%, about 4%, about 5%, 6%, about 7%, about 8%, about 9%, or about 10% by weight.

In some embodiments, the powder comprises about 5% by weight by weight of the AP-based agent; about 87% by weight of the polymer (e.g., HPMCAS-HF); about 2% by weight of the buffer (e.g., monosodium phosphate monohydrate); about 0.06% by weight of the zinc (e.g., zinc sulfate heptahydrate); about 0.5% by weight of the magnesium (e.g., magnesium sulfate heptahydrate); and about 5% by weight the protein stabilizer (e.g., trehalose).

In some embodiments, the powder comprises about 5% by weight by weight of the AP-based agent; about 87.45% by weight of the polymer (e.g., HPMCAS-HF); about 2% by weight of the buffer (e.g., monosodium phosphate monohydrate); about 0.06% by weight of the zinc (e.g., zinc sulfate heptahydrate); about 0.49% by weight of the magnesium (e.g., magnesium sulfate heptahydrate); and about 5% by weight the protein stabilizer (e.g., trehalose).

In various embodiments, the modified-release formulation of the invention is in the form of tablets or capsules. In some embodiments, the modified-release formulation is in the form of tablets or capsules comprising the powders of the invention. A variety of approaches for generating tablets or capsules may be utilized to include powders of the invention. In some embodiments, tablets of the invention are generated by granulation such as dry granulation. In such embodiments, the powders are precompressed and the resulting tablet or slug is milled to yield granules. Alternatively, the powders are precompressed with pressure rolls to yield granules. In yet other embodiments, the powders are encapsulated into capsules. In an embodiment, the capsule is a gelatin capsule, such as a hard gelatin capsule. In another embodiment, the capsule is a hydroxypropyl methylcellulose (HPMC) capsule.

In various embodiments, the tablets or capsules comprise a delayed-release coating that includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In an embodiment, the delayed-release coating includes the enteric agent EUDRAGIT® L 100. In some embodiments, the tablet or capsule is coated with the enteric agent at a coating weight of about 1-20% such as about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%.

Administration and Dosage

It will be appreciated that the actual dose of the AP-based agent to be administered according to the present invention will vary according to, for example, the particular dosage form and the mode of administration. Many factors that may modify the action of the AP-based agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the AP-based agent can be administered in unit dosage forms (e.g., powders, capsules, or tablets) containing, for example, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, or from about 0.1 mg to about 1 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween. In an embodiment, individual dose of the AP-based agent is administered in an unit dosage form containing 150 mg of the AP-based agent. In another embodiment, individual dose of the AP-based agent is administered in an unit dosage form containing 280 mg of the AP-based agent.

In one embodiment, the AP-based agent is administered at an amount of from about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.01 mg to about 100 mg daily, from about 0.01 mg to about 95 mg daily, from about 0.01 mg to about 90 mg daily, from about 0.01 mg to about 85 mg daily, from about 0.01 mg to about 80 mg daily, from about 0.01 mg to about 75 mg daily, from about 0.01 mg to about 70 mg daily, from about 0.01 mg to about 65 mg daily, from about 0.01 mg to about 60 mg daily, from about 0.01 mg to about 55 mg daily, from about 0.01 mg to about 50 mg daily, from about 0.01 mg to about 45 mg daily, from about 0.01 mg to about 40 mg daily, from about 0.01 mg to about 35 mg daily, from about 0.01 mg to about 30 mg daily, from about 0.01 mg to about 25 mg daily, from about 0.01 mg to about 20 mg daily, from about 0.01 mg to about 15 mg daily, from about 0.01 mg to about 10 mg daily, from about 0.01 mg to about 5 mg daily, from about 0.01 mg to about 3 mg daily, from about 0.01 mg to about 1 mg daily, or from about 100 mg to about 300 mg daily.

In various embodiments, the AP-based agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1,000 mg, inclusive of all values and ranges therebetween.

In some embodiments, a suitable dosage of the AP-based agent is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg body weight, inclusive of all values and ranges therebetween. In other embodiments, a suitable dosage of the AP-based agents in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the AP-based agent may be administered, for example, about once per day, about every other day, about every third day, about once a week, about once every two weeks, about once every month, about once every two months, about once every three months, about once every six months, or about once every year. In certain embodiments, the AP-based agent may be administered more than once daily, for example, about two times, about three times, about four times, about five times, about six times, about seven times, about eight times, about nine times, or about ten times daily.

Assays

Dissolution/pH Test

It is important to design the tablet formulation to release in its targeted area of the body. For example, solubility is a critical parameter for informing formulation strategies and extrapolating performance in humans. A disintegration assay in various pH levels may be performed using a disintegration apparatus combined with biologically relevant buffers (e.g., Fasted State Simulated Intestinal Fluid (FaSSIF) and Fasted State Simulated Gastric Fluid (FaSSGF)) for uncoated tablets in order to assess the dissolution rate of the various tablet formulations as described herein. FaSSIF is a buffer that simulates fasting conditions in the small intestine, resulting in a pH representative to values measured from the mid-duodenum to the proximal ileum, usually in the range of pH 4-7. FaSSGF is a buffer that simulates fasting conditions in the stomach, usually pH 1.6.

Dissolution rate is the percent of active ingredient released over time from the tablet. Tablets may exhibit fast-release, or "burst," release profiles, for example 78% release in 15 minutes and 87% release at 60 minutes. Tablets may exhibit a sustained release profile, or an intermediate release profile that falls between sustained release and burst release profiles. Dissolution tests may also be performed on enterically coated tablets. Disintegration assays at a single pH level may be performed using a disintegration apparatus combined with biologically relevant buffer, such as FaSSIF for 90 minutes. Disintegration assays at various pH levels may be performed using a disintegration apparatus combined with biologically relevant buffers, such as FaSSGF for 2 hours, followed by addition of FaSSIF, with a pH adjustment to pH 5.5 for 45 minutes, and finally, with an additional pH adjustment to pH 6.5 for 2-3 hours.

Friability

Friability refers to the tendency of a solid substance to break into smaller pieces under duress or contact, and is important because determining the friability of a formulated tablet will yield information as to the durability of the tablet to remain intact prior to administration. A friability assay may be performed on the tablets of the formulations described herein in order to test the resilience of the tablets in terms of destruction and subsequent weight loss of the tablets in response to simulated pan coating conditions and how compression forces affect the structural stability of the tablets.

Dispersibility

The dispersibility of a powder in water is its ability to break down into particles passing through a sieve. A powder sample of known water content may be spread evenly on the surface of 25° C. water. The mixture is then stirred manually for a short time and part of the mixture is filtered through a sieve. The total solids content of the collected liquid is determined. Dispersibility is calculated from the mass of the test portion and the values for water content and total solids.

Alkaline Phosphatase Activity

In order to test alkaline phosphatase enzyme activity, assays known to those in the art can be performed. For example, an endpoint AP activity assay and/or a kinetic AP activity assay can be used.

Endpoint IAP Activity Assay

An endpoint AP activity assay utilizes purified alkaline phosphatase as a standard by which the activity of samples assayed are quantified. AP solution can also be used as an indicative control. Samples are tested using 2 replicate wells from which S.D. values are generated. Briefly, various samples are dissolved in Sodium dihydrogen phosphate buffer ($NaH_2PO_4$ 50 mM+$ZnSO_4$ 0.5 mM, pH 7.0). A standard curve of AP concentrations of the Sigma standard ranging from 0-20 nM is prepared alongside the AP samples. 80 µl of samples or standards are added to the wells of a flat bottomed 96-well plate, followed by 50 µl of 5 mM pNPP solution. The plate is then incubated for one hour at 25° C. in a light protected environment. After one hour, 20 µl of stop solution is added to each well, then the OD at $A_{405}$ is read in a plate reader, and concentrations are derived through comparison to the standard curve generated through a linear fit trend line, the Y=X equation of which is used to calculate concentration values.

Kinetic IAP Activity Assay

A kinetic AP activity assay utilizes purified alkaline phosphatase as a control to test the activity of samples assayed. AP solution can also be used as an indicative control. Briefly, various samples are dissolved in diethanolamine based buffer (pH 9.8 at 37° C.), and after five minutes of pre-incubation at 37° C., are combined with a 5 mM solution of p-nitrophenyl phosphate (pNPP). After an additional 10 minutes, the colorimetric output at 405 nm as a function of pNPP→NPP dephosphorylation via enzyme phosphatase activity is measured every 20 seconds over 5 minutes using a plate reader. This provides a readout of enzyme kinetics over this time period, the slope of which can be converted to enzyme activity using the substrate extinction coefficient (18.5 $OD_{405}$ units/mM*cm pathlength) or which can be compared to the slope generated from the AP standard.

Stability in Chyme

In order to assess AP-based agent stability in chyme, samples of AP-based agents are incubated in human chyme at 37 C. Stability is then evaluated by assessing aliquots withdrawn from the incubated samples at 0, 0.5, 1, 2, 3, 4, 5, and 6 hours for AP activity using a pNPP AP substrate (absorbance is read at 405 nm using a plate reader). Different chyme specimens can be used for evaluation of stability, including mixed chyme samples. Chyme samples are characterized for pH, liquid content, and protease activity.

Methods of Treatment

Without wishing to be bound by theory, it is believed that AP-based agent including alkaline phosphatases (e.g., IAPs) play a key role in many GI and systemic processes including, for example, participating in intestinal defense, mediating anti-inflammatory functions, maintaining normal gut microflora profiles, maintaining mucosal barrier integrity, and regulating digestion and nutrient (fat) absorption. Accordingly, the present invention provides the use of AP-based agents in a broad-range of therapeutic applications for modulating immune functions, metabolic functions, and neurological functions. In various embodiments, the present invention provides for the treatment of microbiome-related disorders, GI dysbiosis, GI inflammation, colitis (e.g., ulcerative colitis), metabolic diseases (e.g., metabolic syndrome, obesity, and diabetes), neurological diseases (e.g., multiple sclerosis), cystic fibrosis, sepsis, and renal failure with an AP, including, without limitation a pharmaceutical composition comprising an AP-based agent, such as the modified release formulations described herein.

In various aspects, the present invention provides methods for modulating and protecting a subject's GI microbiome, comprising administering an effective amount of a pharmaceutical composition comprising an AP-based agent (and/or additional therapeutic agents) to the subject. In some embodiments, methods of the invention may be used to treat subjects with reduced levels and/or function of GI tract flora by administering an AP-based agent of the invention so as to increase or preserve the number of commensal bacteria and composition of the GI microbiome. In other embodiments, methods of the invention relate to treating infections by pathogenic bacteria and/or inhibiting the growth or decrease the number of pathogenic bacteria in the GI tract.

In various embodiments, the methods of the invention comprise treating or preventing a microbiome-mediated disorder. Illustrative microbiome-mediated disorder includes, but are not limited to, for example, those found in Table 3 of WO 2014/121298, the entire contents of which are incorporated herein by reference. For example, the methods described can be used to treat symptoms associated with reduced levels of commensal bacteria and/or function of GI tract flora, e.g., antibiotic-associated diarrhea (AAD), *Clostridium difficile*-associated disease (CDAD), inflammatory disorders, acquired immunodeficiency syndrome (AIDS) including HIV-mediated gut dysbiosis and GI barrier dysfunctions, hypothyroidism, and obesity.

In various aspects, the present invention provides pharmaceutical compositions comprising an AP-based agent of the invention (and/or additional therapeutic agents) for use in treating an antibiotic-induced adverse effect in the GI tract and/or prevention or treatment of CDI and/or a CDAD in a subject in need thereof. Without wishing to be bound by theory, it is believed that AP-based agent of the invention mediates NTP dephosphorylation which promotes the growth of commensal bacteria in preference to pathologic bacteria and hasten the recovery from antibiotic-induced dysbiosis. Accordingly, treatment with the AP-based agents of the invention has the potential to protect from CDI and enteric gram negative pathogens. In various embodiments, the antibiotic-induced adverse effect and/or CDI or CDAD e is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

In various embodiments, the subjects include, but are not limited to, subjects that are at a particular risk for a microbiome-mediated disorder, such as, by way of non-limiting example, those undergoing treatment or having recently undergone treatment with an antibiotic. For example, the subject may have taken an antibiotic during the past about 30 or so days and/or have an immune system that is weak (e.g. from a chronic illness) and/or is a women and/or is elderly (e.g. over about 65 years old) and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary emergent infection and/or a hospital acquired infection (HAI).

In various embodiments, the present invention provides methods for treating antibiotic-induced adverse effects in the GI tract, comprising administration of an effective amount of an alkaline phosphatase of the invention (and/or additional therapeutic agents) to a subject in need thereof. In another embodiment, the present invention provides methods for preventing an antibiotic-induced adverse effect in the GI tract, comprising an effective amount of an alkaline phosphatase of the invention (and/or additional therapeutic agents) to a subject in need thereof.

In various embodiments, the alkaline phosphatase of the invention protects the intestinal microbiome from antibiotics-induced damage. In an embodiment, the AP-based agent protects the intestinal microbiome from cephalosporin-induced damage. In some embodiment, the AP-based agent of the invention protects the intestinal microbiome from ceftriaxone (CRO)-induced damage. In some embodiments, the methods of the invention treat or prevent an antibiotics-associated adverse effect including but not limited to diarrhea, nausea, vomiting, dysgeusia, colitis, and pseudomembranous colitis disease and/or symptoms. In an embodiment, methods of the invention can be used to treat or prevent antibiotic-associated diarrhea (AAD).

In various embodiments, the present invention provides for compositions and methods for treating infections by pathogenic bacteria and/or inhibiting the growth or decrease the number of pathogenic bacteria in the GI tract. In various embodiments, the present invention provides for compositions and methods that mitigate or prevent the overgrowth of various coliforms in a patient's gut (including coliforms that are virulent and/or antibiotic resistant). Illustrative coliforms include *Citrobacter, Enterobacer, Hafnia, Klebsiella*, and *Escherichia*. In various aspects, the methods and compositions described herein prevent or diminish secondary infections with resistant organisms. In an embodiment, the pathogenic bacteria is an enterobacteria such as *Salmonella*.

In various embodiments, the present invention provides methods for treating or preventing CDI and/or a CDAD, comprising administering an effective amount of an alkaline phosphatase of the invention a subject in need thereof. In an embodiment, the present invention provides methods for preventing CDI and/or a CDAD, comprising administering an effective amount of administering an effective amount of an alkaline phosphatase of the invention to a subject in need thereof (by way of non-limiting example, a patient that is being administered or will be administered an antibiotic).

In some embodiments, the invention relates to a method of preventing CDI and/or a CDAD, comprising administering an effective amount of an alkaline phosphatase of the invention to a subject in need thereof, wherein the subject is undergoing therapy with a primary antibiotic. A "primary antibiotic" refers to an antibiotic that is administered to a patient and which may result in CDI and/or CDAD. These include the antibiotics that most often lead to CDI and/or CDAD: e.g., fluoroquinolones, cephalosporins, clindamycin and penicillins.

In various embodiments, the CDI and/or CDAD is treated or prevented in the context of initial onset or relapse/recurrence (e.g. due to continued or restarted antibiotic therapy). For example, in a patient that has previously suffered from CDI, the present alkaline phosphatase may be administered upon the first symptoms of recurrence. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, CDI and/or CDAD may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, CDI and/or CDAD may also be diagnosed via enzyme immunoassays, e.g., to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLUMIGENE LAMP assay), a cell cytotoxicity assay. For example, any of the following tests may be used: Meridian ImmunoCard Toxins A/B; Wampole Toxin A/B Quik Chek; Wampole C. diff Quik Chek Complete; Remel Xpect *Clostridium difficile* Toxin A/B; Meridian Premier Toxins A/B; Wampole *C. difficile* Tox A/B II; Remel Prospect Toxin A/B EIA; Biomerieux Vidas *C. difficile* Toxin A&B; BD Geneohm C. diff; Prodesse Progastro CD; and Cepheld Xpert C. diff. In various embodiments, the clinical sample is a patient stool sample. Also a flexible sigmoidoscopy "scope" test and/or an abdominal X-ray and/or a computerized tomography (CT) scan, which provides images of your colon, may be used in assessing a patient (e.g. looking for characteristic creamy white or yellow plaques adherent to the wall of the colon). Further, biopsies (e.g. of any region of the GI tract) may be used to assess a potential CDI and/or CDAD patient.

In some embodiments, the methods and uses of the present invention include those in which an initial and/or adjunctive therapy is administered to a subject. Initial and/or adjunctive therapy indicates therapy that is used to treat, for example, a microbiome-mediated disorder or disease upon detection of such disorder or disease. In an embodiment, initial and/or adjunctive therapy indicates therapy that is used to treat CDI and/or CDAD upon detection of such disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy. In various embodiments, the methods and uses of the present invention include use of the alkaline phosphatase as an adjuvant to any of these initial and/or adjunctive therapies (including co-administration or sequential administration). In various embodiments, the methods and uses of the present invention include administration of the AP-based agent described herein to a subject undergoing initial and/or adjunctive therapies.

In various embodiments, the alkaline phosphatase of the invention is administered to a subject who suffers from an increased mucosal permeability of the GI tract. In some embodiments, increased mucosal permeability of the GI tract is the result of a decreased perfusion or ischemia of the intestines. Ischemia, or a lack of oxygen supply by the bloodstream, may be caused by, for example, heart failure, congenital heart disease, congestive heart failure, coronary heart disease, ischemic heart disease, injuries, trauma or surgery. In an embodiment, the AP-based agent is administered to a subject who suffers from leaky gut syndrome.

In some embodiments, the increased mucosal permeability of the GI tract is associated with or caused by autoimmune and inflammatory bowel diseases (IBD), for example, Celiac's disease, Crohn's disease, and colitis (e.g., ulcerative colitis). Accordingly, in some embodiments, the present invention provides methods for treating or preventing autoimmune and IBD, for example, Celiac disease, Crohn's disease, acute radiation enteropathy, chronic delayed radiation enteropathy, proctitis, and colitis (e.g., ulcerative colitis), comprising administering an effective amount of an AP-based agent of the invention to a subject in need thereof. IBD is a group of inflammatory conditions of the large intestine and, in some cases, the small intestine. The main forms of IBD are Crohn's disease and ulcerative colitis (UC). IBD also includes collagenous colitis, lymphocytic colitis, ischemic colitis, diversion colitis, Behçet's syndrome, infective colitis, and indeterminate colitis.

In some embodiments, the present invention provides methods of treating Celiac disease. In some embodiments, the present invention provides methods of treating GI disorders associated with Celiac disease. Celiac disease is an autoimmune disorder that can occur in genetically predisposed people where the ingestion of gluten leads to damage in the small intestine. Individuals with celiac disease have increased intestinal permeability, which allows gluten breakdown products (the triggering antigens of Celiac disease) to reach gut-associated lymphoid tissue, thus initiating an inflammatory response including inflammatory cytokine release and T-cell recruitment. Celiac disease is characterized by chronic inflammation of the small intestinal mucosa that may result in atrophy of the small intestinal villi and diverse symptoms, such as malabsorption, diarrhea, abdominal pain, bloating, fatigue, and nausea. In various embodiments, methods of the invention effectively treat one or more symptoms of Celiac disease including GI symptoms, abdominal symptoms, and non-GI symptoms.

Methods for measuring the improvement in one or more symptoms of Celiac disease can include assessment of the lactulose-to-mannitol (LAMA) ratio, which is an experimental biomarker of intestinal permeability (Kelly et al., (2012) Aliment Pharmacol Ther 2013; 37: 252-262, the entire disclosure is hereby incorporated by reference); measurement of anti-transglutaminase antibody levels; and assessment of clinical symptoms using the Celiac Disease Patient Reported Outcome (CeD PRO), Gastrointestinal Symptom Rating Scale (GSRS), Celiac Disease Gastrointestinal Symptom Rating Scale (CeD GSRS), Bristol Stool Form Scale (BSFS), General Well-Being Questionnaire, Short Form 12 Health Survey Version 2 (SF12V2), Celiac Disease Quality of Life Questionnaire (CeD-QoL), and Clinician Global Assessment of Disease Activity (CGA) as disclosed, for example, in WO/2015/154010, the entire disclosure of which is hereby incorporated by reference. In various embodiments, the present methods of treating Celiac disease provide for a therapeutic effect as assessed by one or more of these measurements.

In some embodiments, the present methods treat Celiac disease and allow a subject to introduce gluten into their diet without substantial symptoms.

In some embodiments, the increased mucosal permeability of the GI tract is associated with or caused by Acquired Immunodeficiency Syndrome (AIDS). Accordingly, in some embodiments, the present invention provides methods of treating GI disorders associated with AIDS. GI disorders are among the most frequent complaints in patients with human immunodeficiency virus 1 (HIV-1) or human immunodeficiency virus 2 (HIV-2)-associated AIDS. GI manifestations of HIV disease include diarrhea, dysphagia, odynophagia, nausea, vomiting, weight loss, abdominal pain, anorectal disease, jaundice, hepatomegaly, GI tract bleeding, and GI tumors (e.g., Kaposi's sarcoma and non-Hodgkin's lymphoma).

Progressive HIV infection often results in GI tract damage, microbial translocation, inflammation, and immune activation which drive progression of disease to AIDS. The term "HIV enteropathy" has been used to describe changes in mucosal structure and function associated with gut-mediated immune dysfunction, as well as to denote the clinical syndrome of chronic diarrhea without an identified infectious cause. In addition to chronic diarrhea, HIV enteropathy is often characterized by increased GI inflammation, increased intestinal permeability, and malabsorption of bile acids and vitamin B12—abnormalities that are thought to be due to direct or indirect effects of HIV on the enteric mucosa (Brenchley J M, Douek D C. Mucosal Immunol 2008; 1:23-30). Clinical consequences include decreased fat and carbohydrate absorption, a trend toward decreased small-bowel transit time, and jejunal atrophy. In various embodiments, methods of the invention effectively treat the symptomatic effects of HIV enteropathy. In various embodiments, methods of the invention prevent, slow, or reverse the progression of HIV infection to AIDS. In various embodiments, methods of the invention prevent or slow the progression of AIDS to death.

Further still, the HIV-1 subtype that a subject becomes infected with may be a factor in the rate of progression to AIDS. In various embodiments, the present methods effectively treat a patient infected with HIV-1 subtype C, D, and G. In another embodiment, the present methods effectively treat a patient infected with HIV-1 subtype A.

In some embodiments, the present invention provides methods of treating various GI disorders associated with HIV infection and/or AIDS. For example, the present invention provides methods of treating HIV-mediated gut dysbiosis and GI barrier dysfunctions, which in various embodiments, may be caused by the HIV, the antibiotics administered to the HIV infected subject, and/or the medications being administered to the HIV infected subject. For example, the HIV infected subject may be taking one or more nucleoside analogues such as deoxyadenosine analogues (e.g., didanosine, vidarabine), adenosine analogues (e.g., BCX4430), deoxycytidine analogues (e.g., cytarabine, emtricitabine, lamivudine, zalcitabine), guanosine and deoxyguanosine analogues (e.g., abacavir, aciclovir, entecavir), thymidine and deoxythymidine analogues (e.g., stavudine, telbivudine, zidovudine), and deoxyuridine analogues (e.g., idoxuridine, trifluridine). In some embodiments, the HIV infected subject may be taking one or more drugs of the highly active anti-retroviral therapy (HAART) regimen. Exemplary HAART medications include entry inhibitors or fusion inhibitors (e.g., maraviroc, enfuvirtide), nucleoside reverse transcriptase inhibitors (NRTI) and nucleotide reverse transcriptase inhibitors (NtRTI) such as the nucleoside and nucleotide analogues described herein, non-nucleoside reverse transcriptase inhibitors (e.g., nevirapine, efavirenz, etravirine, rilpivirine), integrase inhibitors (e.g., raltegravir), and protease inhibitors (e.g., lopinavir, indinavir, nelfinavir, amprenavir, ritonavir, darunavir, atazanavir).

In various embodiments, the present methods reduce local inflammation, alter composition of the GI microbiota, enhance clearance of products of microbial translocation from the circulation, and repair enterocyte barrier in an HIV infected subject and/or a subject having AIDS. In an embodiment, the present methods reduce GI tract damage and gut dysbiosis in an HIV infected subject and/or a subject having AIDS. For example, the present methods may reverse the changes in GI microbiota observed in HIV infected subjects or subjects having AIDS. By way of example, these changes in GI microbiota that may be reversed by the present methods include an altered microbiota featuring increased pathobionts such as *Staphylococcus* spp., *Pseudomonas* spp., Enterobacteriaceae family members with pro-inflammatory potential, as well as enteropathogenic bacteria that catabolize tryptophan into kynurenine derivatives (including *Pseudomonas, Xanthomonas, Bacillus,* and *Burkholderia* spp.) In an embodiment, the present methods reduce GI barrier dysfunctions in an HIV infected subject and/or a subject having AIDS. For example, the present methods may reverse the increased intestinal permeability (e.g., leaky gut syndrome) in an HIV infected subject and/or a subject having AIDS. In an embodiment, the present methods reduce microbial translocations or translocations of microbial products and inflammatory mediators (e.g., LPS) into the systemic circulation in an HIV infected subject and/or a subject having AIDS. In such methods, the levels of LPS, EndoCAb, sCD14, and I-FABP in the subject's plasma may be reduced. In an embodiment, the present methods reduce immune activation and inflammation (e.g., local and systemic immune activation and inflammation) in an HIV infected subject and/or a subject having AIDS. For example, the present methods may decrease inflammation in the gut-associated lymphoid tissue (GALT) and increase the number of CD4+ cells and Th17 cells. The present methods may further inhibit the release of cytotoxic T cells as well as the production of inflammatory mucosal cytokines and markers such as interferon-α, tumor necrosis factor-α, CRP, IL-1β, IL-2, IL4, IL-6 and IL-13.

In some embodiments, the present invention provides methods for treating or preventing dysbiosis and GI dysfunction in patients with cystic fibrosis (CF). The genetic disease CF is associated with mutations in the CF transmembrane conductance regulator (CFTR), which regulates epithelial cell ion and water permeability. In some embodiments, the present methods are used to treating a subject who is homozygous for one or more mutations in the CFTR gene. In some embodiments, the subject is heterozygous for one or more mutations in the CFTR gene. In some embodiments, the one or more CFTR mutations are nonsense mutations. In some embodiments, the one or more CFTR mutations are gating mutations. In some embodiments, the one or more CFTR mutations are protein processing mutations. In some embodiments, the one or more CFTR mutations are conductance mutations. In some embodiments, the one or more CFTR mutations are translation mutations. Examples of CFTR mutations include, but are not limited to, F508del, G542X, G85E, R334W, Y122X, G551D, R117H, A455E, S549R, R553X, V520F, R1162X, R347H, N1203K, S549N, R347P, R560T, G1244E, G1349D, G178R, G551S, S1251N, S1255P, S549R, S1255X, Add9T, Y1092X, M1191K, W 1282X, 3659delC, 394delTT, 3905insT, 1078delT, delta 1507, 3876delA, 2184delA, 2307insA, 711+1G>T, 1717-1G>A, 2789+5G>A, 1898+5G>T, 3120+1G>A, 621+1G>T, 3849+l0kbC>T, 1898+1G>A, 2183 AA>G, and/or 5/7/9T. In various embodiments, methods of the invention are used to treat a CF patient having one or more of the CFTR mutations disclosure herein. In an embodiment, the patient has one or more of the following CFTR mutations: G551D, G1244E, G1349D, G178R, G551S, S1251N, S1255P, S549N, S549R and/or R117H. In an embodiment, the patient has a F508del mutation. Methods for screening a patient's genotype for CFTR mutations are known and may be carried out by, for example, DNA sequencing such as bidirectional sequencing.

CF patients often exhibit symptoms including chronic respiratory infections and dysfunction at GI mucosal surfaces, resulting insubstantial morbidity and mortality. One of the earliest manifestations of CF is GI dysfunction including severe and recurrent intestinal obstruction as well as nutrient malabsorption, which result in growth failure. CF patients also exhibit GI dysbiosis such as an overabundance of *E. coli* in the fecal microbiota and a decrease in the relative abundance of *Bifidobacterium* species. In various embodiments, methods of the invention effectively treat one or more GI-related symptoms of in CF patients.

Methods for measuring change and/or improvement in GI tract function can include, but are not limited to: endoscopy for direct examination of epithelium and mucosa; histological evaluation and/or tissue procurement for direct evaluation of structural changes and/or immune biomarkers; urine tests for assessment of permeability with non-absorbable sugars and LPS levels; stool tests for assessment of inflammation and/or microbiota changes (for example by PCR); and/or blood tests for assessment of specific markers, including CD4+ cell counts, Th17 cell counts, and/or LPS levels.

In some embodiments, the present invention provides methods of treating GI disorders associated with hypothyroidism. Hypothyroidism is a condition in which the thyroid gland does not produce enough thyroid hormone (thyroxine or T4). Often, hypothyroidism slows the actions of the digestive tract causing constipation, or the digestive tract may stop moving entirely. Methods of the invention may alleviate the one or more GI symptoms associated with hypothyroidism.

In one aspect, the present invention provides methods for preventing or treating necrotizing enterocolitis (NEC). The present methods comprise administering to a subject in need thereof an AP-based agent as described herein or a pharmaceutical composition or a formulation such as a modified-release formulation as described herein.

In various embodiments, methods of the invention relate to a pediatric subject for the prevention or treatment of NEC. In various embodiments, the pediatric subject may be from about 1 day to about 1 week old, from about 1 week to about 1 month old, from about 1 month to about 12 months old, from about 12 months to about 18 months old, from about 18 to about 36 months old, from about 1 to about 5 years old, from about 5 to about 10 years old, from about 10 to about 15 years old, or from about 15 to about 18 years old. In some embodiments, the pediatric subject is an infant of about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or about 12 months of age. In various embodiments, the pediatric subject is feeding on formula and/or milk. In various embodiments, the pediatric subject is undergoing treatment or has recently undergone treatment with an antibiotic.

In various embodiments, the pediatric subject is a premature infant. In some embodiments, the premature infant is born at less than 37 weeks of gestational age. In some embodiments, the premature infant is born at about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, or about 37 weeks of gestational age. In other embodiments, the pediatric subject is a full term infant, for example, an infant who is born later than about 37 weeks of gestational age. In some embodiments, the pediatric subject may exhibit one or more of prenatal asphyxia, shock, sepsis, or congenital heart disease. In various embodiments, the pediatric subject is of low birth weight. In various embodiments, the pediatric subject weighs less than about 5 pounds, about 4 pounds, about 3 pounds, or about 2 pounds.

In various embodiments, methods of the invention relate to a pregnant woman for the prevention or treatment of NEC. In some embodiments, the pregnant woman is undergoing treatment or has recently undergone treatment with an antibiotic.

The presence and severity of NEC is graded using the staging system of Bell et al., *J. Ped. Surg.*, 15:569 (1980) as follows: In various embodiments, the present methods treat disease at any of these stages.

Stage I Systemic manifestations—temperature instability, lethargy, apnea, bradycardia
(Suspected NEC) Gastrointestinal manifestations—poor feeding, increased pregavage residuals, emesis (may be bilious or test positive for occult blood), mild abdominal distention, occult blood in stool (no fissure)
Non-specific or normal radiological signs
Stage II Above signs and symptoms plus persistent occult or gross gastrointestinal bleeding, marked abdominal distention
(Definite NEC) Abdominal radiographs showing significant intestinal distention with ileus, small-bowel separation (edema in bowel wall or peritoneal fluid), unchanging or persistent "rigid" bowel loops, pneumatosis intestinalis, portal venous gas
(NEC) Laboratory changes (thrombocytopenia, metabolic acidosis)
Stage III Above signs and symptoms plus deterioration of vital signs, evidence of septic shock, or marked gastrointestinal hemorrhage, hypotension, striking abdominal distension, peritonitis
(Advanced NEC) Abdominal radiographs showing pneumoperitoneum in addition to findings listed for Stage II
Additional laboratory changes (metabolic and respiratory acidosis, disseminated intravascular coagulation)

In various embodiments, methods of the invention effectively treat one or more symptoms of NEC including any of the symptoms described above as well as those symptoms known in the art, including GI symptoms, abdominal symptoms, and non-GI symptoms. In various embodiments, methods of the invention effectively prevent the development of NEC in a subject such as a pediatric subject. In various embodiments, methods of the invention effectively prevent progression of NEC in a subject such as a pediatric subject, for example, from stage I to stage II or from stage II to stage III. In various embodiments, methods of the invention effectively result in regression of NEC in a subject such as a pediatric subject, for example, from stage III to stage II or stage I to complete cure, or from stage II to stage I or to complete cure.

Intestinal dysbiosis is associated with the development of NEC and can be detected in a subject prior to any clinical evidence of the disease. In various embodiments, methods of the invention effectively restore normal microbiota in the intestinal tract of the treated subject. In some embodiments, methods of the invention maintain a normal microbiota in the intestinal tract. For instance, in some embodiments, the methods of the invention maintain a healthy balance (e.g. a healthy ratio and/or healthy distribution) of intestinal microbiota of a subject. In another embodiment, the methods of the invention treat or prevent the overgrowth of one or more pathogenic microorganisms in the GI tract. In certain embodiments, methods of the invention effectively reduce the levels of *Clostridium butyricum* and/or *Clostridium perfringens* in the intestinal tract.

Methods for measuring the improvement in one or more symptoms of NEC include diagnostic imaging modalities such as X-ray and ultrasonography. Methods for measuring change and/or improvement in GI tract function can include, but are not limited to: endoscopy or colonoscopy for direct examination of epithelium and mucosa; histological evaluation and/or tissue procurement for direct evaluation of structural changes and/or immune biomarkers; stool tests for assessment of inflammation and/or microbiota changes (for example by PCR); and/or blood tests for assessment of specific markers and cells.

In some embodiments, the present invention provides methods of treating or preventing metabolic syndrome, diabetes, hypertension, cardiovascular disease, nonalcoholic fatty liver and other metabolic diseases. In various embodiments, the metabolic syndrome is associated with elevated triglycerides, elevated low density lipoproteins, reduced high density lipoproteins, reduced lipoprotein index, elevated fasting glucose levels, elevated fasting insulin, reduced glucose clearance following feeding, insulin resistance, impaired glucose tolerance, obesity and combinations thereof. For example, the present methods may be used to treat subjects having metabolic syndrome and having abdominal obesity (e.g., waist circumference of 40 inches or above in men or 35 inches or above in women), a blood triglyceride level of 150 mg/dL or greater, HDL of less than 40 mg/dL in men or less than 50 mg/dL in women, systolic blood pressure of 130 mm Hg or greater or diastolic blood pressure of 85 mm Hg or greater and/or fasting glucose of 100 mg/dL or greater. Additional metabolic diseases that may be treated using methods of the invention include those described in US2013/0251701, US2011/0206654, and US2004/0115185, the entire contents of which are hereby incorporated by reference.

In an embodiment, the metabolic disease is obesity. Early exposure to antibiotics (e.g. within about the first 2 years of life) can disrupt the microbiome and lead to eventual disease. Bailey, et al. *JAMA Pediatr.* 168(11), November 2014, the entire contents of which are hereby incorporated by reference, describes how early exposure to antibiotics is linked to obesity. Accordingly, in some embodiments, the present methods protect the microbiome of a child and prevent diseases such as obesity. In addition, a shift in the ratio between bacterial divisions Firmicutes and Bacteroidetes is often observed in obese individuals. Accordingly, in some embodiments, the present invention provides methods for treating or preventing obesity by administering an AP agent of the invention. Methods of the invention retain a normal diversity of bacteria in the intestinal tract, such as for example, Bacteroidetes, Proteobacteria, and Firmicutes, thereby treating or preventing obesity. Further still, alkaline phosphatases may influence fat absorption at the GI tract. Accordingly, in various embodiments, the present invention provides methods for treating or preventing obesity by limiting GI fat absorption. In various embodiments, methods of the invention are effective for inducing weight loss or preventing weight gain. In some embodiments, the subjects may have undertaken or will undertake a surgery of the digestive system; be greater than about 80-100 pounds overweight; have a BMI of greater than about 35 kg/m$^2$; or have a health problem related to obesity. In some embodiments, the subjects may have dyslipidemia including hyperlipidemia and hyperlipoproteinemia.

In another embodiment, the metabolic disease is diabetes. In various embodiments, the present invention relates to the treatment for diabetes (type 1 or type 2) and/or glucose intolerance. In some embodiments, the present invention relates to a method for treating subjects at risk of diabetes, one or more of insulin resistance, prediabetes, impaired fasting glucose (IFG), and impaired glucose tolerance (IGT).

In various embodiments, the present invention relates to the treatment of type 1 diabetes with AP, including the formulations described herein. Type 1 diabetes, once known as juvenile diabetes or insulin-dependent diabetes, is a chronic condition in which the pancreas produces little or no insulin. Treatment is often via intensive insulin regimens, which attempt to mimic the body's normal pattern of insulin secretion, and often involve basal and bolus insulin coverage. For example, one common regimen is the administration of a long-acting insulin (including, for example, glargine/detemir) once or twice a day with rapid acting insulin (including, for example, aspart, glulisine, lispro) preprandially or postprandially and as needed to correct high blood sugars (as monitored by a glucose meter, for example). Doses administered preprandially or postprandially or as needed to correct high blood sugars may be referred to as bolus administrations. Another common regimen involves dosing, including continuous dosing, via an insulin pump (or continuous subcutaneous insulin infusion device (CSII)) of, for example a rapid acting insulin (as described herein and including, for example, aspart, glulisine, lispro). In various embodiments, AP, including the formulations described herein, may replace any of the insulins used in various regimens, including instances in which the insulins are not providing effective therapy in the patient. AP, including the formulations described herein, may cause an increase in patient compliance as it may allow for easier self-dosing relative to various forms of insulin, which must be administered as various doses throughout the day—even in the context of an insulin pump, which requires programming. Further, AP, including the formulations described herein, can offset common frustration of diabetic patient dosing, such as, for example, the dawn phenomenon. Alternatively, AP, including the formulations described herein, may be used adjuvant to any of the type 1 diabetes treatments described herein to, for example, normalize a patient's regimen and avoid blood sugar "dips" (e.g. hypoglycemia, e.g. blood sugar of below about 70 mg/dL) and "spikes" (e.g. hyperglycemia, e.g. blood sugar of greater than about 200 mg/dL) that afflict many patients. Accordingly, in some embodiments, AP, including the formulations described herein, may treat or prevent symptoms associated with hypoglycemia, including for example, shakiness, anxiety, nervousness, palpitations, tachycardia, pallor, coldness, clamminess, dilated pupils (mydriasis), hunger, borborygmus, nausea, vomiting, abdominal discomfort, headache, abnormal mentation, impaired judgment, nonspecific dysphoria, paresthesia, negativism, irritability, belligerence, combativeness, rage, personality change, emotional lability, fatigue, weakness, apathy, lethargy, daydreaming, sleep, confusion, amnesia, lightheadedness or dizziness, delirium, staring, "glassy" look, blurred vision, double vision, flashes of light in the field of vision, automatism, difficulty speaking, slurred speech, ataxia, incoordination, focal or general motor deficit, paralysis, hemiparesis, paresthesia, headache, stupor, coma, abnormal breathing, generalized or focal seizures, memory loss, CNS damage (e.g. cognitive impairment), amnesia, and death. Accordingly, in some embodiments, AP, including the formulations described herein, may treat or prevent symptoms associated with hyperglycemia, including for example, polyphagia, polydipsia, polyuria, blurred vision, fatigue, weight loss, poor wound healing, dry mouth, dry or itchy skin, tingling in feet or heels, erectile dysfunction, recurrent infections, external ear infections (e.g. swimmer's ear), cardiac arrhythmia, stupor, coma, and seizures. In various regimens, a type 1 diabetes patient may receive additional agents to supplement insulin therapy. In some embodiments, AP, including the formulations described herein, are used in this manner. AP, including the formulations described herein, may provide additional therapeutic benefits in patients that are struggling to manage type 1 diabetes with insulin therapy alone. In some embodiments, patients that are struggling to manage type 1 diabetes with insulin therapy alone have poor glycemic control as described herein.

In some embodiments, AP, including the formulations described herein, finds use in reducing a patient's blood glucose level to below about 10 mM, e.g. within the range of about 4 mM to about 7 mM.

In some aspects, the present invention provides a method for treating type 1 or type 2 diabetes, comprising administering an effective amount of AP, including the formulations described herein.

In a number of embodiments, including those in which AP, including the formulations described herein, prevents diabetes and/or treats a pre-diabetic condition, a patient is at risk of diabetes if the patient is characterized by one or more of: being physically inactive; having a parent or sibling with diabetes; having a family background associated with high incidence of diabetes, selected from that is African American, Alaska Native, American Indian, Asian American, Hispanic/Latino, or Pacific Islander American; giving birth to a baby weighing more than 9 pounds; being diagnosed with gestational diabetes; having high blood pressure of about 140/90 mmHg or above; being treated for high blood pressure; having HDL cholesterol level below about 35 mg/dL and/or a triglyceride level above about 250 mg/dL; having polycystic ovary syndrome (PCOS); and having cardiovascular disease.

In various embodiments, AP, including the formulations described herein, may be used to treat diabetes in the context of hospitalization. For example, in some embodiments, AP, including the formulations described herein, may be administered to a patient that is in a diabetic coma. In some embodiments, the patient may be administered to a patient that has one or more of a severe diabetic hypoglycemia, advanced diabetic ketoacidosis (e.g. advanced enough to result in unconsciousness, contributing factors may include one or more of hyperglycemia, dehydration, shock, and exhaustion), hyperosmolar nonketotic coma (e.g. with one or more of hyperglycemia and dehydration are contributing factors). In these embodiments, AP, including the formulations described herein, may be used in conjunction with standard treatment regimens of diabetic comas, including administering one or more of glucose, glucagon, insulin, fluids (e.g. saline with potassium and/or other electrolytes), any of which, optionally, are administered intravenously. In some embodiments, AP, including the formulations described herein, may replace insulin in these treatment regimens and, optionally, is administered orally.

Further, in various embodiments pertaining to diabetes, the patient may be receiving or there may be co-administration with one or more additional agents. Illustrative additional agents include insulin or any anti-diabetic agents (e.g. biguanides, insulin secretogogues such as sulphonylureas or meglitinides, inhibitors of α-glucosidase, thiazolidinediones, and others). The methods of treatment described herein, in various embodiments may comprise administering AP, including the formulations described herein, to a patient that is receiving one or more additional agents and/or non-insulin diabetes agents. Additional agents include one or more of a sulfonylurea (e.g. DYMELOR (acetohexamide), DIABINESE (chlorpropamide), ORINASE (tolbutamide), and TOLINASE (tolazamide), GLUCOTROL (glipizide), GLUCOTROL XL (extended release), DIABETA (glyburide), MICRONASE (glyburide), GLYNASE PRESTAB (glyburide), and AMARYL (glimepiride)); a Biguanide (e.g. metformin (GLUCOPHAGE, GLUCOPHAGE XR, RIOMET, FORTAMET, and GLUMETZA)); a thiazolidinedione (e.g. ACTOS (pioglitazone) and AVANDIA (rosiglitazone); an alpha-glucosidase inhibitor (e.g., PRECOSE (acarbose) and GLYSET (miglitol); a Meglitinide (e.g., PRANDIN (repaglinide) and STARLIX (nateglinide)); a Dipeptidyl peptidase IV (DPP-IV) inhibitor (e.g., JANUVIA (sitagliptin), NESINA (alogliptin), ONGLYZA (saxagliptin), and TRADJENTA (linagliptin)); Sodium-glucose co-transporter 2 (SGLT2) inhibitor (e.g. INVOKANA (canaglifozin)); and a combination pill (e.g. GLUCOVANCE, which combines glyburide (a sulfonylurea) and metformin, METAGLIP, which combines glipizide (a sulfonylurea) and metformin, and AVANDAMET, which uses both metformin and rosiglitazone (AVANDIA) in one pill, KAZANO (alogliptin and metformin), and OSENI (alogliptin plus pioglitazone).

Other additional agents include METFORMIN oral, ACTOS oral, BYETTA subcutaneous, JANUVIA oral, WELCHOL oral, JANUMET oral, glipizide oral, glimepiride oral, GLUCOPHAGE oral, LANTUS subcutaneous, glyburide oral, ONGLYZA oral, AMARYI oral, LANTUS SOLOSTAR subcutaneous, BYDUREON subcutaneous, LEVEMIR FLEXPEN subcutaneous, ACTOPLUS MET oral, GLUMETZA oral, TRADJENTA oral, bromocriptine oral, KOMBIGLYZE XR oral, INVOKANA oral, PRANDIN oral, LEVEMIR subcutaneous, PARLODEL oral, pioglitazone oral, NOVOLOG subcutaneous, NOVOLOG FLEXPEN subcutaneous, VICTOZA 2-PAK subcutaneous, HUMALOG subcutaneous, STARLIX oral, FORTAMET oral, GLUCOVANCE oral, GLUCOPHAGE XR oral, NOVOLOG Mix 70-30 FLEXPEN subcutaneous, GLYBURIDE-METFORMIN oral, acarbose oral, SYMLINPEN 60 subcutaneous, GLUCOTROI XL oral, NOVOLIN R inj, GLUCOTROL oral, DUETACT oral, sitagliptin oral, SYMLINPEN 120 subcutaneous, HUMALOG KWIKPEN subcutaneous, JANUMET XR oral, GLIPIZIDE-METFORMIN oral, CYCLOSET oral, HUMALOG MIX 75-25 subcutaneous, nateglinide oral, HUMALOG Mix 75-25 KWIKPEN subcutaneous, HUMULIN 70/30 subcutaneous, PRECOSE oral, APIDRA subcutaneous, Humulin R inj, Jentadueto oral, Victoza 3-Pak subcutaneous, Novolin 70/30 subcutaneous, NOVOLIN N subcutaneous, insulin detemir subcutaneous, glyburide micronized oral, GLYNASE oral, HUMULIN N subcutaneous, insulin glargine subcutaneous, RIOMET oral, pioglitazone-metformin oral, APIDRA SOLOSTAR subcutaneous, insulin lispro subcutaneous, GLYSET oral, HUMULIN 70/30 Pen subcutaneous, colesevelam oral, sitagliptin-metformin oral, DIABETA oral, insulin regular human inj, HUMULIN N Pen subcutaneous, exenatide subcutaneous, HUMALOG Mix 50-50 KWIKPEN subcutaneous, liraglutide subcutaneous, KAZANO oral, repaglinide oral, chlorpropamide oral, insulin aspart subcutaneous, NOVOLOG Mix 70-30 subcutaneous, HUMALOG Mix 50-50 subcutaneous, saxagliptin oral, ACTOPLUS Met XR oral, miglitol oral, NPH insulin human recomb subcutaneous, insulin NPH and regular human subcutaneous, tolazamide oral, mifepristone oral, insulin aspart protam-insulin aspart subcutaneous, repaglinide-metformin oral, saxagliptin-metformin oral, linagliptin-metformin oral, NESINA oral, OSENI oral, tolbutamide oral, insulin lispro protamine and lispro subcutaneous, pramlintide subcutaneous, insulin glulisine subcutaneous, pioglitazone-glimepiride oral, PRANDIMET oral, NOVOLOG PenFill subcutaneous, linagliptin oral, exenatide microspheres subcutaneous, KORLYM oral, alogliptin oral, alogliptin-pioglitazone oral, alogliptin-metformin oral, and canagliflozin oral.

Other additional agents include Lispro (HUMALOG); Aspart (NOVOLOG); Glulisine (APIDRA); Regular (NOVOLIN R or HUMULIN R); NPH (NOVOLIN N or HUMULIN N); Glargine (LANTUS); Detemir (LEVEMIR); HUMULIN or NOVOLIN 70/30; and NOVOLOG Mix 70/30 HUMALOG Mix 75/25 or 50/50.

In various embodiments, the present invention is used to treat or prevent various neurodegenerative diseases. In some embodiments, the neurodegenerative disease is selected from multiple sclerosis (MS; including, without limitation benign multiple sclerosis, relapsing-remitting multiple sclerosis (RRMS), secondary progressive multiple sclerosis (SPMS), progressive relapsing multiple sclerosis (PRMS), and primary progressive multiple sclerosis (PPMS)), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease).

In various embodiments, the present invention provides methods of treating or preventing sepsis. Sepsis is characterized by a whole-body inflammatory state caused by infection. Sepsis includes the presence of various pus-forming and other pathogenic organisms, or their toxins, in the blood or tissues. In some embodiments, the present invention provides methods of treating or preventing septicemia (blood poisoning), bacteremia, viremia, and/or fungemia. In various embodiments, the present invention treats the various end-organ pathologies associated with sepsis such as hypotension, acute tubular necrosis (ATN) and acute respiratory distress syndrome (ARDS).

In various embodiments, the present invention provides methods of treating or preventing renal failure such as acute renal failure (ARF). Acute renal failure involves an acute loss of kidney function that results in an increase of the serum creatinine level. In acute renal failure, the glomerular filtration rate decreases over days to weeks. As a result, excretion of nitrogenous waste is reduced, and fluid and electrolyte balances cannot be maintained. Patients with acute renal failure are often asymptomatic, and the condition is diagnosed by observed elevations of blood urea nitrogen (BUN) and serum creatinine levels. Complete renal shutdown is present when the serum creatinine level rises by at least 0.5 mg per dL per day and the urine output is less than 400 mL per day (oliguria). The AP-based agents described herein can be used not only in the treatment of renal failure but also to improve renal cases where the renal function is at least partly impaired or reduced.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male. In certain embodiments, the human is a patient with a feeding tube. In certain embodiments, the human is a patient who cannot swallow.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

Additional Therapeutic Agents and Combination Therapy

Administration of the present compositions and formulations comprising the AP-based agent may be combined with additional therapeutic agents. Co-administration of the additional therapeutic agent and the present compositions/formulations may be simultaneous or sequential. Further, the present compositions/formulations may comprise an additional therapeutic agent (e.g. via co-formulation). For example, the additional therapeutic agent and the AP-based agent may be combined into a single formulation. Alternatively, the additional therapeutic agent and the AP-based agent may be formulated separately.

In one embodiment, the additional therapeutic agent and the AP-based agent are administered to a subject simultaneously. The term "simultaneously" as used herein, means that the additional therapeutic agent and the AP-based agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the AP-based agent can be by simultaneous administration of a single formulation (e.g., a formulation comprising the additional therapeutic agent and the alkaline phosphatase) or of separate formulations (e.g., a first formulation including the additional therapeutic agent and a second formulation including the AP-based agent).

In a further embodiment, the additional therapeutic agent and the AP-based agent are administered to a subject simultaneously but the release of the additional therapeutic agent and the alkaline phosphatase from their respective dosage forms (or single unit dosage form if co-formulated) may occur sequentially.

Co-administration does not require the additional therapeutic agent and the AP-based agent to be administered simultaneously, if the timing of their administration is such that the pharmacological activities of the additional therapeutic agent and the AP-based agent overlap in time. For example, the additional therapeutic agent and the AP-based agent can be administered sequentially. The term "sequentially" as used herein means that the additional therapeutic agent and the AP-based agent are administered with a time separation of more than about 60 minutes. For example, the time between the sequential administration of the additional therapeutic agent and the AP-based agent can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the AP-based agent being administered. Either the additional therapeutic agent or the AP-based agent may be administered first.

Co-administration also does not require the additional therapeutic agent and the AP-based agent to be administered to the subject by the same route of administration. Rather, each therapeutic agent can be administered by any appropriate route, for example, parenterally or non-parenterally.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-bacterial agent may be any of the penicillin, cephalosporin, monobactam, and carbapenem antibiotics.

In some embodiments, the additional therapeutic agent is an adjunctive therapy that is used in, for example, the treatment of CDI. In some embodiments, the additional therapeutic agent is metronidazole (e.g. FLAGYL), fidaxomicin (e.g. DIFICID), or vancomycin (e.g. VANCOCIN), rifaximin, charcoal-based binders/adsorbents (e.g. DAV132), fecal bacteriotherapy, probiotic therapy (see, e.g., *Intnat'l J Inf Dis*, 16 (11): e786, the contents of which are hereby incorporated by reference, illustrative probiotics include *Saccharomyces boulardii*; *Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med.* 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometholone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which are incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In some embodiments, the additional therapeutic agent may be an anti-viral agent that includes, but is not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet.

In some embodiments, the additional therapeutic agent may be an agent useful for treating inflammatory bowel disease. For example, the agent may be used for treating colitis (e.g., ulcerative colitis) and Crohn's disease, which include, but are not limited to, vedolizumab (ENTYVIO), tofacitinib (XELJANZ), DIMS 0150 (KAPPAPROCT), golimumab (SIMPONI), adalimumab (HUMIRA) and other anti-TNF therapy.

In some embodiments, the additional therapeutic agent may be an agent useful for treating Celiac disease. Illustrative agents include, but are not limited to, AVX-176 (Avaxia Biologics), Actobiotics (ActoGeniX), CALY-002 (Calypso biotech), HLA-DQ2 antagonists, HLA-DQ2/DQ8 antagonists, tTG inhibitors including ERW1041E (GlaxoSmithKline) and ZED-101/ZED-1227 (Zedira), Larazotide acetate (Alba Therapeutics), Latiglutenase (Alvine Pharmaceuticals), BL-7010 (BioLineRx), and NexVax-2 (ImmmunsanT).

In some embodiments, the additional therapeutic agent may be an agent useful for treating cystic fibrosis. Illustrative agents include, but are not limited to, ivacaftor (KALYDECO; Vertex), lumacaftor/ivacaftor (ORKAMBI; Vertex), VX-152 (Vertex), VX-440 (Vertex), VX-371 (Vertex), nitric oxide, glycerol phenylbutyrate, riociguat (Bayer), recombinant A1PI (Grifols, SA), cysteamine IR, JBT-101 (Corbus Pharmaceuticals), N-91115 (Nivalis Therapeutics), and vancomycin.

In some embodiments, the additional therapeutic agent is an agent useful for treating obesity. Illustrative agents include, but are not limited to, orlistat, lorcaserin, phentermine-topiramate, naltrexone-bupropion, sibutramine, rimonabant, exenatide, pramlintide, phentermine, benzphetamine, diethylpropion, phendimetrazine, bupropion, and metformin. In various embodiments, the additional agent is an agent that that interfere with the body's ability to absorb specific nutrients in food, such as orlistat, glucomannan, and guar gum. Agents that suppress appetite are also among the additional agents, e.g. catecholamines and their derivatives (such as phentermine and other amphetamine-based drugs), various anti-depressants and mood stabilizers (e.g. bupropion and topiramate), anorectics (e.g. dexedrine, digoxin). Agents that increase the body's metabolism are also among the additional agents. In some embodiments, additional agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NKI) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; GLP-1 agonists, SGLT-2 inhibitors, and dipeptidyl peptidase 4 (DPP-4) antagonists. In some embodiments, additional agents may be selected from among amphetamines, benzodiazepines, sulfonyl ureas, meglitinides, thiazolidinediones, biguanides, beta-blockers, ACE inhibitors, diuretics, nitrates, calcium channel blockers, phenlermine, sibutramine, lorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, pioglitazone, rosiglilazone, exenatide, albiglutide, dulaglutide, liraglutide, canagliflozin, dapagliflozin, linagliptin, saxagliptin, vildagliptin, and sitagliptin.

In an embodiment, the additional therapeutic agent is an agent for treating pre-diabetes, diabetes, type II diabetes, insulin resistance, glucose intolerance, or hyperglycemia. Examples of drugs include, but are not limited to, alpha-glucosidase inhibitors, amylin analogs, dipeptidyl peptidase-4 inhibitors, GLP1 agonists, SGLT-2 inhibitors, meglitinides, sulfonylureas, biguanides, thiazolidinediones (TZD), and insulin. Additional examples of such agents include bromocriptine and Welchol. Examples of alpha-glucosidase inhibitors include but are not limited to acarbose and miglitol. An example of an amylin analog is pramlintide. Examples of dipeptidyl peptidase-4 inhibitors include but are not limited to saxagliptin, sitagliptin, vildagliptin, linagliptin, and alogliptin. Examples of GLP-1 agonist include but are not limited to albiglutide, dulaglutide, liraglutide, exenatide, exenatide extended release. Examples of SGT-2 inhibitors include but are not limited to canagliflozin and dapagliflozin. Examples of meglitinides include but are not limited to nateglinide, and repaglinide. Examples of sulfonylureas include but are not limited to chlorpropamide, glimepiride, glipizide, glyburide, tolazamide, and tolbutamide. Examples of biguanides include but are not limited to metformin, Riomet, Glucophage, Glucophage XR, Glumetza. Examples of thiazolidinedione include but are not limited to rosiglitazone and pioglitazone. Examples of insulin include but are not limited to Aspart, Detemir, Glargine, Glulisine, and Lispro. Examples of combination drugs include but are not limited to glipizide/metformin, glyburide/metformin, pioglitazone/glimepiride, pioglitazone/metformin, repaglinide/metformin, rosiglitazone/glimepiride, rosiglitazone/metformin, saxagliptin/metformin, sitagliptin/simvastatin, sitagliptin/metformin, linagliptin/metformin, alogliptin/metformin, and alogliptin/pioglitazone.

Kits

The invention provides kits that can simplify the administration of the modified-release formulation described herein. The kit is an assemblage of materials or components, including at least one of the modified-release formulations described herein. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat a disorder associated described herein. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

EXAMPLES

Example 1. Development of Modified-Release Powder Formulations Comprising cIAP

A powder formulation including calf IAP was produced. To produce the powders, cIAP and hypromellose acetate succinate (HPMCAS) polymer were dissolved together in a solvent. The mixture was then spray-dried using spray-dried dispersion (SDD) technology to form powders. Various spray drying conditions were tested. An exemplary spray drying condition utilized for the present invention uses an inlet temperature of 145° C., an outlet temperature of 46° C., and a feed rate of 24 g/min.

The calf IAP formulation comprises IAP co-formulated (by spray-drying) with an excipient mix that provides a compressible powder. The powder provides a more gradual release of IAP into solution and may provide some protection from pepsin degradation in the duodenum. However, as noted in FIG. 1, IAP is very acid sensitive and the excipient co-formulation alone may not protect IAP from the denaturing effects of stomach acid. Consequently, a formulation comprising enteric-coated tablets that prevent IAP release from the stomach and deliver the IAP at different regions of the GI tract is developed. This release profile is achieved by the application of pH-sensitive EUDRAGIT® polymer coatings (Evonik) applied to the tablets at different thicknesses. In some embodiments, tablets coated with EUDRAGIT® L 100 at different coating weight gains (e.g., 6%, 8%, 10% and 15%) were utilized. EUDRAGIT® L 100 dissolves at pH 6.0, and is expected to prevent release of IAP into the stomach and deliver IAP to the jejunum.

An exemplary IAP powder formulation is detailed in Table 1 below. Tablets of the IAP powder (280 mg; 0.3×0.6" oval or 0.35" round) were prepared using a single press at 1000 psi. Evaluation of IAP release in a physiologically appropriate buffer demonstrated that 100% of the IAP activity can be recovered from the tablet if the IAP is protected from acid.

TABLE 1

IAP Powder Formulation

| Ingredient | % by Weight | | | Function |
|---|---|---|---|---|
| | Spray Dry Solution* | Active IAP Powder | Placebo Powder | |
| Calf Intestinal Alkaline Phosphatase | 0.250% | 5.00% | 0.00% | API |
| HPMCAS—HF† | 4.372% | 87.45% | 92.05% | Polymer matrix |
| Zinc Sulfate Heptahydrate | 0.003% (0.1 mM) | 0.06% | 0.06% | Enzyme co-factor |
| Magnesium Sulfate Heptahydrate | 0.025% (1.0 mM) | 0.49% | 0.52% | Enzyme co-factor |
| Monosodium phosphate monohydrate | 0.100% | 2.00% | 2.11% | Buffer |
| Trehalose | 0.250% | 5.00% | 5.26% | Protein stabilizer (drying) |
| DI Water | 95.000% | — | — | Solvent |

*Spray drying conditions: inlet temperature 145° C.; outlet temperature 46° C.; feed rate 24 g/min.
†Hydroxypropylmethylcellulose acetate succinate (also called hypromellose acetate succinate)

In another exemplary tablet formulation, the IAP powder formulation may be mixed with additional excipients to improve processing parameters such as flowability and improve tablet features such as hardness and friability. In one example, Active IAP Powder from Table 1 (50% of final tablet weight) is mixed with magnesium stearate (1%), silicon dioxide (0.5%), Ac-Di-Sol (also called crosscarmellose sodium, 1%) and microcrystalline cellulose (47.5%). Tablets (250 mg; 1 cm cross section) are formed by compression of the mixture using standard concave tooling to a final hardness of 9 kp with <0.1% friability.

Example 2. Modified-Release Powder Formulations Comprising cIAP Exhibit Disintegration Profile A visual disintegration study was conducted on tablets containing about 88% HPMCAS-HF with or without 5% disintegrant. The tablets were tested under disintegration conditions in Fasted State Simulated Intestinal Fluid at pH 6.5 until the tablets were no longer visible. The results showed that the tablets containing about 88% HPMCAS-HF took about 90 minutes to disintegrate, and IAP activity was retained from about 70-90%.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., AP-based agents and/or additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A formulation comprising an alkaline phosphatase (AP), being in the form of a tablet, comprising:
   about 1-10% by weight AP,
   about 80-95% by weight polymer, wherein the polymer is hypromellose acetate succinate (HPMCAS),
   about 1-10% by weight buffer,
   about 0.01-0.1% by weight zinc,
   about 0.1-1% by weight magnesium stearate, and
   about 1-10% by weight protein stabilizer,
   wherein the formulation is compressible and releases the AP in the intestines.

2. The formulation of claim 1, wherein the AP is released in the small intestine.

3. The formulation of claim 1, wherein the AP is released in the large intestine.

4. The formulation of claim 1, wherein the tablet transforms into a gel in the presence of stomach acid.

5. The formulation of claim 1, wherein the tablet further comprises a poly(methacrylic acid, methylmethacrylate) polymer.

6. The formulation of claim 1, wherein the tablet comprises:
   about 5% by weight AP,
   about 87% by weight polymer, wherein the polymer is hypromellose acetate succinate (HPMCAS),
   about 2% by weight buffer;
   about 0.05% by weight zinc;
   about 0.5% by weight magnesium stearate; and
   about 5% by weight protein stabilizer.

7. The formulation of claim 1, wherein the tablet comprises:
   5% by weight AP,
   87.45% by weight polymer, wherein the polymer is hypromellose acetate succinate (HPMCAS),
   2% by weight buffer;
   0.06% by weight zinc;
   0.49% by weight magnesium stearate; and
   5% by weight protein stabilizer.

* * * * *

SEQUENCE LISTING

<160> NUMBER OF SEQ ID NOS: 37

<210> SEQ ID NO 1
<211> LENGTH: 528
<212> TYPE: PRT
<213> ORGANISM: Artificial Sequence
<220> FEATURE:

<223> OTHER INFORMATION: Synthetic polypeptide

<400> SEQUENCE: 1

```
Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
        35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Arg Phe Asn Gln Cys Asn Thr Thr Arg
130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
370                 375                 380

Gly Tyr Thr Leu Arg Gly Ser Ser Ile Phe Gly Leu Ala Pro Ser Lys
385                 390                 395                 400
```

-continued

```
Ala Gln Asp Ser Lys Ala Tyr Thr Ser Ile Leu Tyr Gly Asn Gly Pro
            405                 410                 415

Gly Tyr Val Phe Asn Ser Gly Val Arg Pro Asp Val Asn Glu Ser Glu
        420                 425                 430

Ser Gly Ser Pro Asp Tyr Gln Gln Gln Ala Ala Val Pro Leu Ser Ser
    435                 440                 445

Glu Thr His Gly Gly Glu Asp Val Ala Val Phe Ala Arg Gly Pro Gln
450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525
```

<210> SEQ ID NO 2
<211> LENGTH: 533
<212> TYPE: PRT
<213> ORGANISM: Artificial Sequence
<220> FEATURE:
<223> OTHER INFORMATION: Synthetic polypeptide

<400> SEQUENCE: 2

```
Met Gln Gly Ala Cys Val Leu Leu Leu Gly Leu His Leu Gln Leu
1               5                   10                  15

Ser Leu Gly Leu Ile Pro Ala Glu Glu Asn Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Ala Arg Tyr Asn Gln Cys Asn Thr Thr Arg
    130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205

Leu Val Tyr Asn Met Asp Ile Asp Val Ile Leu Gly Gly Gly Arg Met
    210                 215                 220

Tyr Met Phe Pro Glu Gly Thr Pro Asp Pro Glu Tyr Pro Asp Asp Ala
225                 230                 235                 240
```

```
Ser Val Asn Gly Val Arg Lys Asp Lys Gln Asn Leu Val Gln Glu Trp
            245                 250                 255
Gln Ala Lys His Gln Gly Ala Gln Tyr Val Trp Asn Arg Thr Ala Leu
        260                 265                 270
Leu Gln Ala Ala Asp Ser Ser Val Thr His Leu Met Gly Leu Phe
        275                 280                 285
Glu Pro Ala Asp Met Lys Tyr Asn Val Gln Asp His Thr Lys Asp
290                 295                 300
Pro Thr Leu Ala Glu Met Thr Glu Ala Ala Leu Gln Val Leu Ser Arg
305                 310                 315                 320
Asn Pro Arg Gly Phe Tyr Leu Phe Val Glu Gly Gly Arg Ile Asp His
                325                 330                 335
Gly His His Asp Gly Lys Ala Tyr Met Ala Leu Thr Glu Ala Ile Met
            340                 345                 350
Phe Asp Asn Ala Ile Ala Lys Ala Asn Glu Leu Thr Ser Glu Leu Asp
        355                 360                 365
Thr Leu Ile Leu Val Thr Ala Asp His Ser His Val Phe Ser Phe Gly
    370                 375                 380
Gly Tyr Thr Leu Arg Gly Thr Ser Ile Phe Gly Leu Ala Pro Gly Lys
385                 390                 395                 400
Ala Leu Asp Ser Lys Ser Tyr Thr Ser Ile Leu Tyr Gly Asn Gly Pro
                405                 410                 415
Gly Tyr Ala Leu Gly Gly Gly Ser Arg Pro Asp Val Asn Gly Ser Thr
            420                 425                 430
Ser Glu Glu Pro Ser Tyr Arg Gln Gln Ala Ala Val Pro Leu Ala Ser
        435                 440                 445
Glu Thr His Gly Gly Glu Asp Val Ala Val Phe Ala Arg Gly Pro Gln
    450                 455                 460
Ala His Leu Val His Gly Val Gln Glu Glu Thr Phe Val Ala His Ile
465                 470                 475                 480
Met Ala Phe Ala Gly Cys Val Glu Pro Tyr Thr Asp Cys Asn Leu Pro
                485                 490                 495
Ala Pro Ala Thr Ala Thr Ser Ile Pro Asp Ala Ala His Leu Ala Ala
            500                 505                 510
Ser Pro Pro Leu Ala Leu Leu Ala Gly Ala Met Leu Leu Leu Leu
        515                 520                 525
Ala Pro Thr Leu Tyr
    530

<210> SEQ ID NO 3
<211> LENGTH: 530
<212> TYPE: PRT
<213> ORGANISM: Artificial Sequence
<220> FEATURE:
<223> OTHER INFORMATION: Synthetic polypeptide

<400> SEQUENCE: 3

Met Gln Trp Ala Cys Val Leu Leu Leu Gly Leu Trp Leu Gln Leu
1               5                   10                  15
Ser Leu Thr Phe Ile Pro Ala Glu Glu Glu Asp Pro Ala Phe Trp Asn
            20                  25                  30
Arg Gln Ala Ala Gln Ala Leu Asp Val Ala Lys Lys Leu Gln Pro Ile
        35                  40                  45
Gln Thr Ala Ala Lys Asn Val Ile Leu Phe Leu Gly Asp Gly Met Gly
    50                  55                  60
```

-continued

```
Val Pro Thr Val Thr Ala Thr Arg Ile Leu Lys Gly Gln Met Asn Gly
 65                  70                  75                  80

Lys Leu Gly Pro Glu Thr Pro Leu Ala Met Asp Gln Phe Pro Tyr Val
                 85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
```

```
                        485                 490                 495
Ala Pro Ser Gly Leu Ser Asp Ala Ala His Leu Ala Ala Ser Pro Pro
                    500                 505                 510

Ser Leu Ala Leu Leu Ala Gly Ala Met Leu Leu Leu Leu Ala Pro Ala
            515                 520                 525

Leu Tyr
    530

<210> SEQ ID NO 4
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 4

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
        35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
    290                 295                 300

Pro Ser Leu Met Glu Met Thr Glu Ala Ala Leu Arg Leu Leu Ser Arg
```

```
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
                340                 345                 350

Phe Asp Asp Ala Ile Glu Arg Ala Gly Gln Leu Thr Ser Glu Glu Asp
                355                 360                 365

Thr Leu Thr Leu Val Thr Ala Asp His Ser His Val Phe Ser Phe Gly
            370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
                420                 425                 430

Ser Gly Ser Pro Asp Tyr Gln Gln Gln Ala Ala Val Pro Leu Ser Ser
            435                 440                 445

Glu Thr His Gly Gly Glu Asp Val Ala Val Phe Ala Arg Gly Pro Gln
        450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Gly Thr Thr Asp
                500

<210> SEQ ID NO 5
<211> LENGTH: 506
<212> TYPE: PRT
<213> ORGANISM: Artificial Sequence
<220> FEATURE:
<223> OTHER INFORMATION: Synthetic polypeptide

<400> SEQUENCE: 5

Met Gln Gly Ala Cys Val Leu Leu Leu Gly Leu His Leu Gln Leu
1               5                   10                  15

Ser Leu Gly Leu Ile Pro Ala Glu Glu Glu Asn Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Arg Thr
            115                 120                 125

Ile Gly Val Ser Ala Ala Arg Tyr Asn Gln Cys Asn Thr Thr Arg
        130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
```

165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205

Leu Val Tyr Asn Met Asp Ile Asp Val Ile Leu Gly Gly Arg Met
210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
        275                 280                 285

Glu Pro Ala Asp Met Lys Tyr Asn Val Gln Gln Asp His Thr Lys Asp
    290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
        355                 360                 365

Thr Leu Ile Leu Val Thr Ala Asp His Ser His Val Phe Ser Phe Gly
    370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu Gly Gly Gly Ser Arg Pro Asp Val Asn Gly Ser Thr
            420                 425                 430

Ser Glu Glu Pro Ser Tyr Arg Gln Gln Ala Ala Val Pro Leu Ala Ser
        435                 440                 445

Glu Thr His Gly Gly Glu Asp Val Ala Val Phe Ala Arg Gly Pro Gln
    450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp
            500                 505

<210> SEQ ID NO 6
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 6

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn

-continued

```
             20                  25                  30
Arg Gln Ala Ala Gln Ala Leu Asp Val Ala Lys Lys Leu Gln Pro Ile
             35                  40                  45
Gln Thr Ala Ala Lys Asn Val Ile Leu Phe Leu Gly Asp Gly Met Gly
             50                  55                  60
Val Pro Thr Val Thr Ala Thr Arg Ile Leu Lys Gly Gln Met Asn Gly
 65                  70                  75                  80
Lys Leu Gly Pro Glu Thr Pro Leu Ala Met Asp Gln Phe Pro Tyr Val
                     85                  90                  95
Ala Leu Ser Lys Thr Tyr Asn Val Asp Arg Gln Val Pro Asp Ser Ala
                 100                 105                 110
Gly Thr Ala Thr Ala Tyr Leu Cys Gly Val Lys Gly Asn Tyr Lys Thr
             115                 120                 125
Ile Gly Val Ser Ala Ala Arg Tyr Asn Gln Cys Asn Thr Thr Ser
             130                 135                 140
Gly Asn Glu Val Thr Ser Val Met Asn Arg Ala Lys Lys Ala Gly Lys
145                 150                 155                 160
Ser Val Gly Val Val Thr Thr Ser Arg Val Gln His Ala Ser Pro Ala
                 165                 170                 175
Gly Ala Tyr Ala His Thr Val Asn Arg Asn Trp Tyr Ser Asp Ala Asp
             180                 185                 190
Leu Pro Ala Asp Ala Gln Thr Tyr Gly Cys Gln Asp Ile Ala Thr Gln
             195                 200                 205
Leu Val Asn Asn Met Asp Ile Asp Val Ile Leu Gly Gly Gly Arg Met
             210                 215                 220
Tyr Met Phe Pro Glu Gly Thr Pro Asp Pro Glu Tyr Pro Tyr Asp Val
225                 230                 235                 240
Asn Gln Thr Gly Val Arg Lys Asp Lys Arg Asn Leu Val Gln Glu Trp
                 245                 250                 255
Gln Ala Lys His Gln Gly Ala Gln Tyr Val Trp Asn Arg Thr Glu Leu
             260                 265                 270
Leu Gln Ala Ala Asn Asp Pro Ser Val Thr His Leu Met Gly Leu Phe
             275                 280                 285
Glu Pro Ala Asp Met Lys Tyr Asn Val Gln Gln Asp Pro Thr Lys Asp
             290                 295                 300
Pro Thr Leu Glu Glu Met Thr Glu Ala Ala Leu Gln Val Leu Ser Arg
305                 310                 315                 320
Asn Pro Gln Gly Phe Tyr Leu Phe Val Glu Gly Gly Arg Ile Asp His
                 325                 330                 335
Gly His His Glu Gly Lys Ala Tyr Met Ala Leu Thr Asp Thr Val Met
             340                 345                 350
Phe Asp Asn Ala Ile Ala Lys Ala Asn Glu Leu Thr Ser Glu Leu Asp
             355                 360                 365
Thr Leu Ile Leu Ala Thr Ala Asp His Ser His Val Phe Ser Phe Gly
             370                 375                 380
Gly Tyr Thr Leu Arg Gly Thr Ser Ile Phe Gly Leu Ala Pro Ser Lys
385                 390                 395                 400
Ala Ser Asp Asn Lys Ser Tyr Thr Ser Ile Leu Tyr Gly Asn Gly Pro
                 405                 410                 415
Gly Tyr Val Leu Gly Gly Gly Leu Arg Pro Asp Val Asn Asp Ser Ile
             420                 425                 430
Ser Glu Asp Pro Ser Tyr Arg Gln Gln Ala Ala Val Pro Leu Ser Ser
             435                 440                 445
```

```
Glu Ser His Gly Gly Glu Asp Val Ala Val Phe Ala Arg Gly Pro Gln
    450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp
            500

<210> SEQ ID NO 7
<211> LENGTH: 508
<212> TYPE: PRT
<213> ORGANISM: Artificial Sequence
<220> FEATURE:
<223> OTHER INFORMATION: Synthetic polypeptide

<400> SEQUENCE: 7

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300
```

```
Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Arg Ile Asp His
            325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
            405                 410                 415

Gly Tyr Val Leu Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
450                 455                 460

Ala His Leu Val His Gly Val Gln Glu Thr Phe Val Ala His Val
465                 470                 475                 480

Met Ala Phe Ala Gly Cys Val Glu Pro Tyr Thr Asp Cys Asn Leu Pro
            485                 490                 495

Ala Pro Ser Gly Leu Ser Asp Ala Ala His Leu Ala
            500                 505
```

<210> SEQ ID NO 8
<211> LENGTH: 754
<212> TYPE: PRT
<213> ORGANISM: Artificial Sequence
<220> FEATURE:
<223> OTHER INFORMATION: Synthetic polypeptide

<400> SEQUENCE: 8

```
Met Gln Gly Ala Cys Val Leu Leu Leu Gly Leu His Leu Gln Leu
1               5                   10                  15

Ser Leu Gly Leu Ile Pro Ala Glu Glu Glu Asn Pro Ala Phe Trp Asn
            20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
            85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
            115                 120                 125

Ile Gly Val Ser Ala Ala Arg Tyr Asn Gln Cys Asn Thr Thr Arg
            130                 135                 140

Gly Asn Glu Val Thr Ser Val Ile Asn Arg Ala Lys Lys Ala Gly Lys
145                 150                 155                 160
```

```
Ala Val Gly Val Val Thr Thr Thr Arg Val Gln His Ala Ser Pro Ala
            165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
            195                 200                 205

Leu Val Tyr Asn Met Asp Ile Asp Val Ile Leu Gly Gly Arg Met
            210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
            245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
            275                 280                 285

Glu Pro Ala Asp Met Lys Tyr Asn Val Gln Gln Asp His Thr Lys Asp
            290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
            325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
            355                 360                 365

Thr Leu Ile Leu Val Thr Ala Asp His Ser His Val Phe Ser Phe Gly
            370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
            405                 410                 415

Gly Tyr Ala Leu Gly Gly Gly Ser Arg Pro Asp Val Asn Gly Ser Thr
            420                 425                 430

Ser Glu Glu Pro Ser Tyr Arg Gln Gln Ala Ala Val Pro Leu Ala Ser
            435                 440                 445

Glu Thr His Gly Gly Glu Asp Val Ala Val Phe Ala Arg Gly Pro Gln
            450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
            485                 490                 495

Ala Pro Ala Thr Ala Thr Ser Ile Pro Asp Gly Gly Ser Gly Gly Ser
            500                 505                 510

Gly Gly Gly Gly Ser Gly Gly Gly Ser Glu Pro Lys Ser Cys Asp
            515                 520                 525

Lys Thr His Thr Cys Pro Pro Cys Pro Ala Pro Glu Leu Leu Gly Gly
            530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser His Glu
            565                 570                 575
```

```
Asp Pro Gln Val Lys Phe Asn Trp Tyr Val Asp Gly Val Gln Val His
                580                 585                 590

Asn Ala Lys Thr Lys Pro Arg Glu Gln Gln Tyr Asn Ser Thr Tyr Arg
            595                 600                 605

Val Val Ser Val Leu Thr Val Leu His Gln Asn Trp Leu Asp Gly Lys
        610                 615                 620

Glu Tyr Lys Cys Lys Val Ser Asn Lys Ala Leu Pro Ala Pro Ile Glu
625                 630                 635                 640

Lys Thr Ile Ser Lys Ala Lys Gly Gln Pro Arg Glu Pro Gln Val Tyr
                645                 650                 655

Thr Leu Pro Pro Ser Arg Glu Glu Met Thr Lys Asn Gln Val Ser Leu
            660                 665                 670

Thr Cys Leu Val Lys Gly Phe Tyr Pro Ser Asp Ile Ala Val Glu Trp
        675                 680                 685

Glu Ser Asn Gly Gln Pro Glu Asn Asn Tyr Lys Thr Thr Pro Pro Val
690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Ala Leu His Asn His Tyr Thr Gln Lys Ser Leu Ser Leu Ser Pro
            740                 745                 750

Gly Lys

<210> SEQ ID NO 9
<211> LENGTH: 751
<212> TYPE: PRT
<213> ORGANISM: Artificial Sequence
<220> FEATURE:
<223> OTHER INFORMATION: Synthetic polypeptide

<400> SEQUENCE: 9

Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
```

```
                 180                 185                 190
Leu Pro Ala Asp Ala Gln Thr Tyr Gly Cys Gln Asp Ile Ala Thr Gln
            195                 200                 205
Leu Val Asn Asn Met Asp Ile Asp Val Ile Leu Gly Gly Arg Met
        210                 215                 220
Tyr Met Phe Pro Glu Gly Thr Pro Asp Pro Glu Tyr Pro Tyr Asp Val
225                 230                 235                 240
Asn Gln Thr Gly Val Arg Lys Asp Lys Arg Asn Leu Val Gln Glu Trp
                245                 250                 255
Gln Ala Lys His Gln Gly Ala Gln Tyr Val Trp Asn Arg Thr Glu Leu
            260                 265                 270
Leu Gln Ala Ala Asn Asp Pro Ser Val Thr His Leu Met Gly Leu Phe
        275                 280                 285
Glu Pro Ala Asp Met Lys Tyr Asn Val Gln Gln Asp Pro Thr Lys Asp
        290                 295                 300
Pro Thr Leu Glu Glu Met Thr Glu Ala Ala Leu Gln Val Leu Ser Arg
305                 310                 315                 320
Asn Pro Gln Gly Phe Tyr Leu Phe Val Glu Gly Gly Arg Ile Asp His
                325                 330                 335
Gly His His Glu Gly Lys Ala Tyr Met Ala Leu Thr Asp Thr Val Met
            340                 345                 350
Phe Asp Asn Ala Ile Ala Lys Ala Asn Glu Leu Thr Ser Glu Leu Asp
        355                 360                 365
Thr Leu Ile Leu Ala Thr Ala Asp His Ser His Val Phe Ser Phe Gly
370                 375                 380
Gly Tyr Thr Leu Arg Gly Thr Ser Ile Phe Gly Leu Ala Pro Ser Lys
385                 390                 395                 400
Ala Ser Asp Asn Lys Ser Tyr Thr Ser Ile Leu Tyr Gly Asn Gly Pro
                405                 410                 415
Gly Tyr Val Leu Gly Gly Gly Leu Arg Pro Asp Val Asn Asp Ser Ile
            420                 425                 430
Ser Glu Asp Pro Ser Tyr Arg Gln Gln Ala Ala Val Pro Leu Ser Ser
        435                 440                 445
Glu Ser His Gly Gly Glu Asp Val Ala Val Phe Ala Arg Gly Pro Gln
        450                 455                 460
Ala His Leu Val His Gly Val Gln Glu Glu Thr Phe Val Ala His Val
465                 470                 475                 480
Met Ala Phe Ala Gly Cys Val Glu Pro Tyr Thr Asp Cys Asn Leu Pro
                485                 490                 495
Ala Pro Ser Gly Leu Ser Asp Gly Gly Ser Gly Gly Ser Gly Gly Gly
            500                 505                 510
Gly Ser Gly Gly Gly Ser Glu Pro Lys Ser Cys Asp Lys Thr His
        515                 520                 525
Thr Cys Pro Pro Cys Pro Ala Pro Glu Leu Leu Gly Gly Pro Ser Val
        530                 535                 540
Phe Leu Phe Pro Pro Lys Pro Lys Asp Thr Leu Met Ile Ser Arg Thr
545                 550                 555                 560
Pro Glu Val Thr Cys Val Val Val Asp Val Ser His Glu Asp Pro Gln
                565                 570                 575
Val Lys Phe Asn Trp Tyr Val Asp Gly Val Gln Val His Asn Ala Lys
            580                 585                 590
Thr Lys Pro Arg Glu Gln Gln Tyr Asn Ser Thr Tyr Arg Val Val Ser
        595                 600                 605
```

Val Leu Thr Val Leu His Gln Asn Trp Leu Asp Gly Lys Glu Tyr Lys
    610                 615                 620

Cys Lys Val Ser Asn Lys Ala Leu Pro Ala Pro Ile Glu Lys Thr Ile
625                 630                 635                 640

Ser Lys Ala Lys Gly Gln Pro Arg Glu Pro Gln Val Tyr Thr Leu Pro
                    645                 650                 655

Pro Ser Arg Glu Glu Met Thr Lys Asn Gln Val Ser Leu Thr Cys Leu
                660                 665                 670

Val Lys Gly Phe Tyr Pro Ser Asp Ile Ala Val Glu Trp Glu Ser Asn
            675                 680                 685

Gly Gln Pro Glu Asn Asn Tyr Lys Thr Thr Pro Pro Val Leu Asp Ser
    690                 695                 700

Asp Gly Ser Phe Phe Leu Tyr Ser Lys Leu Thr Val Asp Lys Ser Arg
705                 710                 715                 720

Trp Gln Gln Gly Asn Val Phe Ser Cys Ser Val Met His Glu Ala Leu
                725                 730                 735

His Asn His Tyr Thr Gln Lys Ser Leu Ser Leu Ser Pro Gly Lys
                740                 745                 750

<210> SEQ ID NO 10
<211> LENGTH: 539
<212> TYPE: PRT
<213> ORGANISM: Artificial Sequence
<220> FEATURE:
<223> OTHER INFORMATION: Synthetic polypeptide

<400> SEQUENCE: 10

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

```
Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
    290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
    370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
    450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Glu
                485                 490                 495

Val Leu Phe Gln Gly Pro Ala Pro Ala Gly Thr Thr Asp Ala Ala
            500                 505                 510

His Pro Gly Arg Ser Val Val Pro Ala Leu Leu Pro Leu Arg Ala Gly
        515                 520                 525

Thr Leu Leu Leu Glu Thr Ala Thr Ala Pro
    530                 535
```

<210> SEQ ID NO 11
<211> LENGTH: 534
<212> TYPE: PRT
<213> ORGANISM: Artificial Sequence
<220> FEATURE:
<223> OTHER INFORMATION: Synthetic polypeptide

<400> SEQUENCE: 11

```
Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45
```

```
Gln Thr Ala Ala Lys Asn Val Ile Leu Phe Leu Gly Asp Gly Met Gly
     50                  55                  60

Val Pro Thr Val Thr Ala Thr Arg Ile Leu Lys Gly Gln Met Asn Gly
 65                  70                  75                  80

Lys Leu Gly Pro Glu Thr Pro Leu Ala Met Asp Gln Phe Pro Tyr Val
                 85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
            115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
            275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
450                 455                 460
```

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Ala
            485                 490                 495

Pro Pro Ala Gly Thr Thr Asp Ala Ala His Pro Ile Glu Gly Arg Ser
        500                 505                 510

Val Val Pro Ala Leu Leu Pro Leu Arg Ala Gly Thr Leu Leu Leu Leu
    515                 520                 525

Glu Thr Ala Thr Ala Pro
    530

<210> SEQ ID NO 12
<211> LENGTH: 1669
<212> TYPE: DNA
<213> ORGANISM: Artificial Sequence
<220> FEATURE:
<223> OTHER INFORMATION: Synthetic polynucleotide

<400> SEQUENCE: 12

| | | | | | |
|---|---|---|---|---|---|
| atgcaggggc | cctgggtgct | gctgctgctg | ggcctgaggc | tacagctctc | cctgggcgtc | 60 |
| atcccaggta | atgaggctcc | ccaagctgtt | ccacacacag | ggcaccccct | cagccaggct | 120 |
| gacctgatct | ctactctccc | cctggccagc | tgaggaggag | aacccggcct | tctggaaccg | 180 |
| ccaggcagct | gaggccctgg | atgctgccaa | gaagctgcag | cccatccaga | aggtcgccaa | 240 |
| gaacctcatc | ctcttcctgg | gcgatgggtt | ggggggtgccc | acggtgacag | ccaccaggat | 300 |
| cctaaagggg | cagaagaatg | gcaaactggg | gcctgagacg | cccctggcca | tggaccgctt | 360 |
| cccataccta | gctctgtcca | agacatacaa | tgtggacaga | caggtgccag | acagcgcagc | 420 |
| cacagccacg | gcctacctgt | gcggggtcaa | ggccaacttc | cagaccatcg | gcttgagtgc | 480 |
| agccgcccgc | tttaaccagt | gcaacacgac | acgcggcaat | gaggtcatct | ccgtgatgaa | 540 |
| ccgggccaag | caagcaggaa | agtcagtagg | agtggtgacc | accacacggg | tgcagcacgc | 600 |
| ctcgccagcc | ggcacctacg | cacacacagt | gaaccgcaac | tggtactcag | atgctgacat | 660 |
| gcctgcctca | gcccgccagg | aggggtgcca | ggacatcgcc | actcagctca | tctccaacat | 720 |
| ggacattgac | gtgatccttg | gcggaggccg | caagtacatg | tttcccatgg | ggacccccaga | 780 |
| ccctgagtac | ccagctgatg | ccagccagaa | tggaatcagg | ctggacggga | agaacctggt | 840 |
| gcaggaatgg | ctggcaaagc | accagggtgc | ctggtatgtg | tggaaccgca | ctgagctcat | 900 |
| gcaggcgtcc | ctggaccagt | ctgtgaccca | tctcatgggc | ctctttgagc | ccggagacac | 960 |
| gaaatatgag | atccaccgag | accccacact | ggacccctcc | ctgatggaga | tgacagaggc | 1020 |
| tgccctgcgc | tgctgagca | ggaaccccc g | cggcttctac | ctctttgtgg | agggcggccg | 1080 |
| catcgaccat | ggtcatcatg | agggtgtggc | ttaccaggca | ctcactgagg | cggtcatgtt | 1140 |
| cgacgacgcc | attgagaggg | cgggccagct | caccagcgag | gaggacacgc | tgaccctcgt | 1200 |
| caccgctgac | cactcccatg | tcttctcctt | tggtggctac | accttgcgag | ggagctccat | 1260 |
| cttcgggttg | gcccccagca | aggctcagga | cagcaaagcc | tacacgtcca | tcctgtacgg | 1320 |
| caatggcccg | ggctacgtgt | tcaactcagg | cgtgcgacca | gacgtgaatg | agagcgagag | 1380 |
| cgggagcccc | gattaccagc | agcaggcggc | ggtgccctg | tcgtccgaga | cccacggagg | 1440 |
| cgaagacgtg | gcggtgtttg | cgcgcggccc | gcaggcgcac | ctggtgcatg | tgtgcagga | 1500 |
| gcagagcttc | gtagcgcatg | tcatggcctt | cgctgcctgt | ctggagccct | acacggcctg | 1560 |
| cgacctggcg | cctcccgcct | gcaccaccga | cgccgcgcac | ccagttgccg | cgtcgctgcc | 1620 |

-continued

```
actgctggcc gggaccctgc tgctgctggg ggcgtccgct gctccctga        1669
```

<210> SEQ ID NO 13
<211> LENGTH: 1671
<212> TYPE: DNA
<213> ORGANISM: Artificial Sequence
<220> FEATURE:
<223> OTHER INFORMATION: Synthetic polynucleotide

<400> SEQUENCE: 13

```
atgcaggggc cctgggtgct gctgctgctg ggcctgaggc tacagctctc cctgggcgtc    60
atcccagctg aggaggagaa cccggccttc tggaaccgcc aggcagctga ggccctggat   120
gctgccaaga agctgcagcc catccagaag gtcgccaaga acctcatcct cttcctgggc   180
gatgggttgg gggtgcccac ggtgacagcc accaggatcc taaaggggca gaagaatggc   240
aaactggggc ctgagacgcc cctggccatg gaccgcttcc catacctggc tctgtccaag   300
acatacaatg tggacagaca ggtgccagac agcgcagcca cagccacggc ctacctgtgc   360
ggggtcaagg ccaacttcca gaccatcggc ttgagtgcag ccgcccgctt taaccagtgc   420
aacacgacac gcggcaatga ggtcatctcc gtgatgaacc gggccaagca agcaggaaag   480
tcagtaggag tggtgaccac cacacgggtg cagcacgcct cgccagccgg cacctacgca   540
cacacagtga accgcaactg gtactcagat gctgacatgc ctgcctcagc ccgccaggag   600
gggtgccagg acatcgccac tcagctcatc tccaacatgg acattgacgt gatccttggc   660
ggaggccgca agtacatgtt tcccatgggg accccagacc ctgagtaccc agctgatgcc   720
agccagaatg gaatcaggct ggacgggaag aacctggtgc aggaatggct ggcaaagcac   780
cagggtgcct ggtatgtgtg gaaccgcact gagctcatgc aggcgtccct ggaccagtct   840
gtgacccatc tcatgggcct ctttgagccc ggagacacga aatatgagat ccaccgagac   900
cccacactgg accctccct gatggagatg acagaggctg ccctgcgcct gctgagcagg   960
aaccccgcg gcttctacct ctttgtggag ggcggccgca tcgaccatgg tcatcatgag  1020
ggtgtggctt accaggcact cactgaggcg gtcatgttcg acgacgccat tgagagggcg  1080
ggccagctca ccagcgagga ggacacgctg accctcgtca ccgctgacca ctcccatgtc  1140
ttctcctttg gtggctacac cttgcgaggg agctccatct tcgggttggc ccccagcaag  1200
gctcaggaca gcaaagccta cacgtccatc ctgtacggca atggcccggg ctacgtgttc  1260
aactcaggcg tgcgaccaga cgtgaatgag agcgagagcg ggagccccga ttaccagcag  1320
caggcggcgg tgcccctgtc gtccgagacc cacggaggcg aagacgtggc ggtgtttgcg  1380
cgcggcccgc aggcgcacct ggtgcatggt gtgcaggagc agagcttcgt agcgcatgtc  1440
atggccttcg ctgcctgtct ggagccctac acggccgcg acctggccgcc tcccgcctgc  1500
accaccgacg ccgcgcaccc agttgccgcg tcgctgccac tgctggccgg gaccctgctg  1560
ctgctggggg cgtccgctgc tcccctgattt actaaaacct tgaaataaaa ttgtaaaaca  1620
tcagtttgaa ggcctgactc tcagggtagt tctttttttaa ttctgggttt t           1671
```

<210> SEQ ID NO 14
<211> LENGTH: 1672
<212> TYPE: DNA
<213> ORGANISM: Artificial Sequence
<220> FEATURE:
<223> OTHER INFORMATION: Synthetic polynucleotide

<400> SEQUENCE: 14

```
atgcagtggg cctgtgtgct gctgctgctg ggcctgtggc tacagctctc cctcaccttc    60
```

```
atcccaggta atcaggcggc tcccagcagc ccctactcac aggggcggct ctaggctgac        120
ctgaccaaca ctctcccctt gggcagctga ggaggaagac cccgccttct ggaaccgcca        180
ggcagcccag gcccttgatg tagccaagaa gttgcagccg atccagacag ctgccaagaa        240
tgtcatcctc ttcttggggg atgggatggg ggtgcctacg gtgacagcca ctcggatcct        300
aaaggggcag atgaatggta agctgggacc tgagacaccc ctggccatgg accagttccc        360
atacgtggct ctgtccaaga catacaacgt ggacagacag gtgccagaca gcgcaggcac        420
tgccactgcc tacctgtgtg gggtcaaggg caactacaaa accattggtg taagtgcagc        480
cgcccgctac aaccagtgca cacaacaag tggcaatgag gtcacgtctg tgatgaaccg        540
ggccaagaaa gcaggaaagt cagtgggagt ggtgaccacc tccagggtgc agcatgcctc        600
cccagccggt gcttatgcac acacggtgaa ccgaaactgg tactcagatg ccgacctgcc        660
tgccgatgca cagacgtatg gctgccagga catcgccaca caactggtca caacatggga        720
tattgacgtg atcctgggtg gaggccgaat gtacatgttt cctgagggga ccccggatcc        780 tgaatacccca tacgatgtca atcagactgg agtccggaag gacaagcgga atctggtgca        840
ggagtggcag gccaagcacc agggagccca gtatgtgtgg aaccgcacgg agctccttca        900
ggcagccaat gaccccagtg taacacacct catgggcctc tttgagccgg cagacatgaa        960
gtataatgtt cagcaagacc ccaccaagga cccgaccctg gaggagatga cggaggcggc       1020
cctgcaagtg ctgagcagga accccagggg cttctacctc ttcgtggagg aggccgcat       1080 tgaccacgt caccatgaag gcaaagctta tatggcactg actgatacag tcatgtttga       1140
caatgccatc gccaaggcta acgagctcac tagcgaactg gacacgctga tccttgccac       1200
tgcagaccac tccatgtctc tctcttttgg tggctacaca ctgcgtggga cctccatttt       1260
cggtctggcc cccagcaagg cctcagacaa caagtcctac acctccatcc tctatggcaa       1320
tggccctggc tacgtgcttg gtgggggctt aaggcccgat gttaatgaca gcataagcga       1380 ggaccctcg tacggcagc aggcggccgt gccctgtct agtgagtccc acggggccga       1440
ggacgtggcg gtgttcgcgc gaggccccgca ggcgcacctg gtgcacggcg tgcaggagga       1500
gaccttcgtg gcgcacgtca tggcctttgc gggctgcgtg gagccctaca ccgactgcaa       1560
tctgccggcc ccctctggcc tctccgacgc cgcgcacctg cggccagcc cgccttcgct       1620 ggcgctgctg gccggggcga tgctgctgct gctggcgcct gccttgtact ga            1672
```

<210> SEQ ID NO 15
<211> LENGTH: 1869
<212> TYPE: DNA
<213> ORGANISM: Artificial Sequence
<220> FEATURE:
<223> OTHER INFORMATION: Synthetic polynucleotide

<400> SEQUENCE: 15

```
atgcagtggg cctgtgtgct gctgctgctg ggcctgtggc tacagctctc cctcaccttc         60
atcccagctg aggaggaaga ccccgccttc tggaaccgcc aggcagccca ggcccttgat        120
gtagccaaga agttgcagcc gatccagaca gctgccaaga atgtcatcct cttcttgggg        180
gatgggatgg gggtgcctac ggtgacagcc actcggatcc taaaggggca gatgaatggt        240
aagctgggac ctgagacacc cctggccatg gaccagttcc catacgtggc tctgtccaag        300
acatacaacg tggacagaca ggtgccagac agcgcaggca ctgccactgc ctacctgtgt        360
ggggtcaagg gcaactacaa aaccattggt gtaagtgcag ccgcccgcta caaccagtgc        420
```

| | | |
|---|---|---|
| aacacaacaa gtggcaatga ggtcacgtct gtgatgaacc gggccaagaa agcaggaaag | 480 |
| tcagtgggag tggtgaccac ctccagggtg cagcatgcct ccccagccgg tgcttatgca | 540 |
| cacacggtga accgaaactg gtactcagat gccgacctgc ctgccgatgc acagacgtat | 600 |
| ggctgccagg acatcgccac acaactggtc aacaacatgg atattgacgt gatcctgggt | 660 |
| ggaggccgaa tgtacatgtt tcctgagggg accccggatc ctgaataccc atacgatgtc | 720 |
| aatcagactg gagtccggaa ggacaagcgg aatctggtgc aggagtggca ggccaagcac | 780 |
| cagggagccc agtatgtgtg gaaccgcacg gagctccttc aggcagccaa tgaccccagt | 840 |
| gtaacacacc tcatgggcct ctttgagccg gcagacatga agtataatgt tcagcaagac | 900 |
| cccaccaagg acccgaccct ggaggagatg acggaggcgg ccctgcaagt gctgagcagg | 960 |
| aaccccagg gcttctacct cttcgtggag ggaggccgca ttgaccacgg tcaccatgaa | 1020 |
| ggcaaagctt atatggcact gactgataca gtcatgtttg acaatgccat cgccaaggct | 1080 |
| aacgagctca ctagcgaact ggacacgctg atccttgcca ctgcagacca ctcccatgtc | 1140 |
| ttctcttttg gtggctacac actgcgtggg acctccattt tcggtctggc ccccagcaag | 1200 |
| gcctcagaca caagtcctca cacctccatc ctctatggca atggccctgg ctacgtgctt | 1260 |
| ggtgggggct taaggcccga tgttaatgac agcataagcg aggaccctc gtaccggcag | 1320 |
| caggcggccg tgcccctgtc tagtgagtcc cacggggggcg aggacgtggc ggtgttcgcg | 1380 |
| cgaggcccgc aggcgcacct ggtgcacggc gtgcaggagg agaccttcgt ggcgcacgtc | 1440 |
| atggcctttg cgggctgcgt ggagccctac accgactgca atctgccggc ccctctggc | 1500 |
| ctctccgacg ccgcgcacct ggcggccagc ccgccttcgc tggcgctgct ggccggggcg | 1560 |
| atgctgctgc tgctggcgcc tgccttgtac tgagggacc cggggggtggg gacacaggcc | 1620 |
| ccgcccctccc tgggaggcag gaagcagctc tcaaataaac tgttctaagt atgatacagg | 1680 |
| agtgatacat gtgtgaagag aagcccttag gtgggggcac agagtgtctg ggtgaggggg | 1740 |
| gtcagggtca catcaggagg ttagggaggg gttgatgaag gctgacgtt gagcaaagac | 1800 |
| caaaggcaac tcagaaggac agtggtgcag gactgggtgt ggtcagcagg gggactggtt | 1860 |
| gggggatcc | 1869 |

```
<210> SEQ ID NO 16
<211> LENGTH: 1260
<212> TYPE: DNA
<213> ORGANISM: Artificial Sequence
<220> FEATURE:
<223> OTHER INFORMATION: Synthetic polynucleotide

<400> SEQUENCE: 16
```

| | | |
|---|---|---|
| aaaaaacaag acaaagctga gatcagaaat gtcattgtga tgataggcga cggcatgggg | 60 |
| acgccttaca taagagccta ccgttccatg aaaaataacg gtgacacacc gaataacccg | 120 |
| aagttaacag aatttgaccg gaacctgaca ggcatgatga tgacgcatcc ggatgaccct | 180 |
| gactataata ttacagattc agcagcagcc ggaacagcat tagcgacagg cgttaagaca | 240 |
| tataacaatg caattggcgt cgataaaaac ggaaaaaaag tgaaatctgt acttgaagag | 300 |
| gccaaacagc aaggcaagtc aacagggctt gtcgccacgt ctgaaattaa ccacgccact | 360 |
| ccagccgcat atggcgccca caatgaatca cggaaaaaca tggaccaaat cgccaacagc | 420 |
| tatatggatg acaagataaa aggcaaacat aaaatagacg tgctgctcgg cggcggaaaa | 480 |
| tcttatttta accgcaagaa cagaaacttg acaaaggaat tcaaacaagc cggctacagc | 540 |
| tatgtgacaa ctaaacaagc attgaaaaaa aataaagatc agcaggtgct cgggcttttc | 600 |

```
gcagatggag ggcttgctaa agcgctcgac cgtgacagta aaacaccgtc tctcaaagac    660
atgacggttt cagcaattga tcgcctgaac caaaataaaa aaggattttt cttgatggtc    720
gaagggagcc agattgactg ggcggcccat gacaatgata cagtaggagc catgagcgag    780
gttaaagatt ttgaacaggc ctataaagcc gcgattgaat ttgcgaaaaa agacaaacat    840
acacttgtga ttgcaactgc tgaccataca accggcggct ttaccattgg cgcaaacggg    900
gaaaagaatt ggcacgcaga accgattctc tccgctaaga aaacctga attcatggcc     960 aaaaaaatca gtgaaggcaa gccggttaaa gatgtgctcg cccgctatgc caatctgaaa   1020
gtcacatctg aagaaatcaa aagcgttgaa gcagctgcac aggctgacaa agcaaaggg   1080 gcctccaaag ccatcatcaa gattttaat acccgctcca acagcggatg gacgagtacc   1140
gatcataccg gcgaagaagt accggtatac gcgtacggcc ccggaaaaga aaattccgc   1200 ggattgatta caatacgga ccaggcaaac atcatattta agattttaa aactggaaaa    1260
```

<210> SEQ ID NO 17
<211> LENGTH: 420
<212> TYPE: PRT
<213> ORGANISM: Artificial Sequence
<220> FEATURE:
<223> OTHER INFORMATION: Synthetic polypeptide

<400> SEQUENCE: 17

```
Lys Lys Gln Asp Lys Ala Glu Ile Arg Asn Val Ile Val Met Ile Gly
1               5                   10                  15

Asp Gly Met Gly Thr Pro Tyr Ile Arg Ala Tyr Arg Ser Met Lys Asn
            20                  25                  30

Asn Gly Asp Thr Pro Asn Asn Pro Lys Leu Thr Glu Phe Asp Arg Asn
        35                  40                  45

Leu Thr Gly Met Met Met Thr His Pro Asp Asp Pro Asp Tyr Asn Ile
    50                  55                  60

Thr Asp Ser Ala Ala Ala Gly Thr Ala Leu Ala Thr Gly Val Lys Thr
65                  70                  75                  80

Tyr Asn Asn Ala Ile Gly Val Asp Lys Asn Gly Lys Lys Val Lys Ser
                85                  90                  95

Val Leu Glu Glu Ala Lys Gln Gln Gly Lys Ser Thr Gly Leu Val Ala
            100                 105                 110

Thr Ser Glu Ile Asn His Ala Thr Pro Ala Ala Tyr Gly Ala His Asn
        115                 120                 125

Glu Ser Arg Lys Asn Met Asp Gln Ile Ala Asn Ser Tyr Met Asp Asp
    130                 135                 140

Lys Ile Lys Gly Lys His Lys Ile Asp Val Leu Leu Gly Gly Gly Lys
145                 150                 155                 160

Ser Tyr Phe Asn Arg Lys Asn Arg Asn Leu Thr Lys Glu Phe Lys Gln
                165                 170                 175

Ala Gly Tyr Ser Tyr Val Thr Thr Lys Gln Ala Leu Lys Lys Asn Lys
            180                 185                 190

Asp Gln Gln Val Leu Gly Leu Phe Ala Asp Gly Gly Leu Ala Lys Ala
        195                 200                 205

Leu Asp Arg Asp Ser Lys Thr Pro Ser Leu Lys Asp Met Thr Val Ser
    210                 215                 220

Ala Ile Asp Arg Leu Asn Gln Asn Lys Lys Gly Phe Phe Leu Met Val
225                 230                 235                 240

Glu Gly Ser Gln Ile Asp Trp Ala Ala His Asp Asn Asp Thr Val Gly
```

```
                245                 250                 255
Ala Met Ser Glu Val Lys Asp Phe Glu Gln Ala Tyr Lys Ala Ala Ile
            260                 265                 270

Glu Phe Ala Lys Lys Asp Lys His Thr Leu Val Ile Ala Thr Ala Asp
        275                 280                 285

His Thr Thr Gly Gly Phe Thr Ile Gly Ala Asn Gly Glu Lys Asn Trp
    290                 295                 300

His Ala Glu Pro Ile Leu Ser Ala Lys Lys Thr Pro Glu Phe Met Ala
305                 310                 315                 320

Lys Lys Ile Ser Glu Gly Lys Pro Val Lys Asp Val Leu Ala Arg Tyr
                325                 330                 335

Ala Asn Leu Lys Val Thr Ser Glu Glu Ile Lys Ser Val Glu Ala Ala
            340                 345                 350

Ala Gln Ala Asp Lys Ser Lys Gly Ala Ser Lys Ala Ile Ile Lys Ile
        355                 360                 365

Phe Asn Thr Arg Ser Asn Ser Gly Trp Thr Ser Thr Asp His Thr Gly
    370                 375                 380

Glu Glu Val Pro Val Tyr Ala Tyr Gly Pro Gly Lys Glu Lys Phe Arg
385                 390                 395                 400

Gly Leu Ile Asn Asn Thr Asp Gln Ala Asn Ile Ile Phe Lys Ile Leu
                405                 410                 415

Lys Thr Gly Lys
            420

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 18

Gly Gly Ser Gly Gly Ser Gly Gly Gly Ser Gly Gly Gly Gly Gly Ser
1               5                   10                  15

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide

<400> SEQUENCE: 19

Gly Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Gly Gly Gly Gly Ser Gly Gly Gly Gly Ser
1               5                   10

<210> SEQ ID NO 21
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 21

Gly Gly Gly Gly Ser Gly Gly Gly Ser Gly Gly Gly Gly Ser
1               5                   10                  15

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Gly Gly Gly Gly Ser Gly Gly Gly Gly Ser Gly Gly Gly Gly Ser Gly
1               5                   10                  15

Gly Gly Gly Ser
            20

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Gly Gly Gly Gly Gly Gly Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Gly Gly Gly Gly Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

Glu Ala Ala Ala Lys
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Glu Ala Ala Ala Lys Glu Ala Ala Ala Lys
1               5                   10

<210> SEQ ID NO 27
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 27

Glu Ala Ala Ala Lys Glu Ala Ala Ala Lys Glu Ala Ala Ala Lys
1               5                   10                  15

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide

<400> SEQUENCE: 28

Ala Glu Ala Ala Ala Lys Glu Ala Ala Ala Lys Ala
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Synthetic peptide

<400> SEQUENCE: 29

Ala Glu Ala Ala Ala Lys Glu Ala Ala Ala Lys Glu Ala Ala Ala Lys
1               5                   10                  15

Ala

<210> SEQ ID NO 30
<211> LENGTH: 22
<212> TYPE: PRT
<213> ORGANISM: Artificial Sequence
<220> FEATURE:
<223> OTHER INFORMATION: Synthetic peptide

<400> SEQUENCE: 30

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 31
<211> LENGTH: 27
<212> TYPE: PRT
<213> ORGANISM: Artificial Sequence
<220> FEATURE:
<223> OTHER INFORMATION: Synthetic peptide

<400> SEQUENCE: 31

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 32
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 32
```

```
Ala Glu Ala Ala Ala Lys Glu Ala Ala Lys Glu Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45
```

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

```
Pro Ala Pro Ala Pro
1               5
```

<210> SEQ ID NO 34
<211> LENGTH: 18
<212> TYPE: PRT
<213> ORGANISM: Artificial Sequence
<220> FEATURE:
<223> OTHER INFORMATION: Synthetic peptide

<400> SEQUENCE: 34

```
Lys Glu Ser Gly Ser Val Ser Ser Glu Gln Leu Ala Gln Phe Arg Ser
1               5                   10                  15

Leu Asp
```

<210> SEQ ID NO 35
<211> LENGTH: 14
<212> TYPE: PRT
<213> ORGANISM: Artificial Sequence
<220> FEATURE:
<223> OTHER INFORMATION: Synthetic peptide

<400> SEQUENCE: 35

```
Glu Gly Lys Ser Ser Gly Ser Gly Ser Glu Ser Lys Ser Thr
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide

<400> SEQUENCE: 36

```
Gly Ser Ala Gly Ser Ala Ala Gly Ser Gly Glu Phe
1               5                   10
```

<210> SEQ ID NO 37
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 37
gccgccacca tgg                                                        13